US008476471B2

(12) United States Patent
Yiannikouros et al.

(10) Patent No.: US 8,476,471 B2
(45) Date of Patent: Jul. 2, 2013

(54) SYNTHESIS OF PROSTANOIDS

(75) Inventors: George Petros Yiannikouros, Florence, SC (US); Panos Kalaritis, Florence, SC (US); Chaminda Priyapushpa Gamage, Florence, SC (US); Stephanie Bosse Abernathy, Florence, SC (US)

(73) Assignee: Irix Pharmaceuticals, Inc., Florence, SC (US)

( * ) Notice: Subject to any disclaimer, the term of this patent is extended or adjusted under 35 U.S.C. 154(b) by 0 days.

(21) Appl. No.: 13/383,764

(22) PCT Filed: Jul. 13, 2010

(86) PCT No.: PCT/US2010/041825
§ 371 (c)(1),
(2), (4) Date: Mar. 15, 2012

(87) PCT Pub. No.: WO2011/008756
PCT Pub. Date: Jan. 20, 2011

(65) Prior Publication Data
US 2012/0165293 A1 Jun. 28, 2012

Related U.S. Application Data

(60) Provisional application No. 61/225,047, filed on Jul. 13, 2009.

(51) Int. Cl.
*C07C 69/74* (2006.01)
(52) U.S. Cl.
USPC ....................................................... 560/121
(58) Field of Classification Search
USPC ....................................................... 560/121
See application file for complete search history.

(56) References Cited

U.S. PATENT DOCUMENTS

| 3,864,387 | A | 2/1975 | Nelson |
| 3,935,240 | A | 1/1976 | Mallion |
| 4,016,184 | A | 4/1977 | Morton, Jr. |
| 4,025,516 | A | 5/1977 | Razdan et al. |
| 4,032,543 | A | 6/1977 | Bundy |
| 4,032,576 | A | 6/1977 | Nelson |
| 4,033,989 | A | 7/1977 | Bundy |
| 4,045,449 | A | 8/1977 | Bundy |
| 4,049,648 | A | 9/1977 | Bundy |
| 4,049,678 | A | 9/1977 | Peterson |
| 4,055,602 | A | 10/1977 | Nelson |
| 4,079,055 | A | 3/1978 | Mallion et al. |
| 4,099,014 | A | 7/1978 | Peterson |
| 4,116,979 | A | 9/1978 | Razdan et al. |
| 4,122,282 | A | 10/1978 | Nelson |
| RE30,053 | E | 7/1979 | Bundy |
| 5,164,412 | A | 11/1992 | Konishi et al. |
| 5,628,984 | A | 5/1997 | Boucher, Jr. |
| 6,262,293 | B1 | 7/2001 | Tani et al. |
| 6,586,468 | B1 | 7/2003 | Maruyama et al. |
| 6,891,062 | B2 | 5/2005 | Oida et al. |
| 6,936,723 | B2 | 8/2005 | De Brabander et al. |
| 7,109,371 | B2 * | 9/2006 | Clissold et al. ............... 560/183 |
| 2005/0154220 | A1 | 7/2005 | Clissold et al. |
| 2005/0282898 | A1 | 12/2005 | Buchwald et al. |
| 2009/0048203 | A1 | 2/2009 | Cavero-Tomas et al. |
| 2009/0259058 | A1 | 10/2009 | Henschke et al. |

FOREIGN PATENT DOCUMENTS

| EP | 0 171 441 | 2/1986 |
| GB | 1 554 023 | 10/1979 |
| JP | 61-011231 | 4/1986 |
| JP | 10-259179 | 9/1998 |
| WO | WO01/57015 | 8/2001 |
| WO | WO02/090324 | 11/2002 |
| WO | WO02/096868 | 12/2002 |
| WO | WO2004/106356 | 12/2004 |
| WO | WO2005/058812 | 6/2005 |
| WO | WO2007/111952 | 10/2007 |
| WO | WO2011/008756 | 1/2011 |

OTHER PUBLICATIONS

Ghosh et al. Factors influencing ring closure through olefin metathesis—A perspective, J. Chem. Sci., vol. 118, No. 3, May 2006, pp. 223-235.*
Dorwald F. A. Side Reactions in Organic Synthesis, 2005, Wiley: VCH, Weinheim p. IX of Preface p. 1-15.*
Pandya et al. Journal of Organic Chemistry, 2008, 73, 3754-3758.*
Sosnowski, et al. Journal of Organic Chemistry, 50(15), 2759-63; 1985.*
"10006692 (+)-15-epi Clo," Cayman Chemical. 1 page <http://www.caymanchem.com/app/template/Product.vm/catalog/10006692> (Accessed on Jun. 17, 2009).
"16768 (+)-Fluprostenol," Cayman Chemical. pp. 1-2 <http://www.caymanchem.com/app/template/Product.vm/catalog/16768> (Accessed on Jun. 17, 2009).
"16814 15(R)-17-phenyl trinor Prostaglandin $F_{2\alpha}$," Cayman Chemical. 1 page <http://www.caymanchem.com/app/template/Product.vm/catalog/16814/tab/data/a/z;jsessio . . . >.
"Bimatoprost," Wikipedia, the free encyclopedia. 1 page <http://en.wikipedia.org/wiki/Bimatoprost> (Accessed on Jun. 17, 2009).
"Carboprost," Wikipedia, the free encyclopedia. 1 page <http://en.wikipedia.org/wiki/Carboprost> (Accessed on Jun. 17, 2009).
"Latanoprost," Wikipedia, the free encyclopedia. 1 page <http://en.wikipedia.org/wiki/Latanoprost> (Accessed on Jun. 17, 2009).
"Limaprost—Compound Summary," PubChem Public Chemical Database. 1 page <http://pubchem.ncbi.nlm.nih.gov/summary/summary.cgi?cid=6438378> (Accessed on Jun. 17, 2009).
"Misoprostol," Wikipedia, the free encyclopedia. pp. 1-6 <http://en.wikipedia.org/wiki/Misoprostol> (Accessed on Jul. 8, 2010).
"Prostacyclin," Wikipedia, the free encyclopedia. pp. 1-5 <http://en.wikipedia.org/wiki/Prostacyclin> (Accessed on Jul. 8, 2010).
"Prostaglandin E1," Wikipedia, the free encyclopedia. pp. 1-2 <http://en.wikipedia.org/wiki/Prostaglandin_E1> (Accessed on Jul. 8, 2010).
"Prostaglandin F2alpha," Wikipedia, the free encyclopedia. 1 page <http://en.wikipedia.org/wiki/Prostaglandin_F2alpha> (Accessed on Jul. 8, 2010).

(Continued)

*Primary Examiner* — Nizal Chandrakumar
(74) *Attorney, Agent, or Firm* — Jenkins, Wilson, Taylor & Hunt, P.A.

(57) ABSTRACT

The presently disclosed subject matter provides a method of synthesizing prostaglandins and prostaglandin analogs comprising the ring closing metathesis of compounds of Formula (I). Also provided are novel compounds of Formula (I) and Formula (II). In addition to their use as synthetic intermediates in the presently disclosed methods, compounds of Formula (II) can be used as prostaglandin and/or prostaglandin analog prodrugs.

22 Claims, No Drawings

OTHER PUBLICATIONS

"Sulprostone," Wikipedia, the free encyclopedia, 1 page <http://en.wikipedia.org/wiki/Sulprostone> (Accessed on Jun. 17, 2009).

"Tafluprost," Wikipedia, the free encyclopedia. 1 page <http://en.wikipedia.org/wiki/Tafluprost> (Accessed on Jun. 17, 2009).

"Travoprost," Wikipedia, the free encyclopedia. 1 page <http://en.wikipedia.org/wiki/Travoprost> (Accessed on Jun. 17, 2009).

"Unoprostone," Wikipedia, the free encyclopedia. 1 page <http://en.wikipedia.org/wiki/Unoprostone> (Accessed on Jun. 17, 2009).

Bundy et al., "Synthesis and Biological Activity of Prostaglandin Lactones," Journal of Medicinal Chemistry. vol. 26, No. 8 pp. 1089-1099 (1983).

Collins, P.W., and Djuric, S.W., "Synthesis of Therapeutically Useful Prostaglandin and Prostacyclin Analogs," Chemical Reviews. vol. 93, No. 4 pp. 1533-1564 (1993).

Fürstner et al., "Novel and Flexible Entries into Prostaglandins and Analogues Based on Ring Closing Alkyne Metathesis of Alkyne Cross Metathesis," J. Am. Chem. Soc. vol. 122, No. 48 pp. 11799-11805 (2000).

Hazato et al., "Synthesis of Thiaprostaglandin $E_1$ Derivatives," Chem. Pharm. Bull. vol. 33, No. 5 pp. 1815-1825 (1985).

Mitsuda et al., "Studies on enantioselective hydrolysis of the acetic ester of a secondary alcohol with *Arthrobacter* lipase," Applied Microbiology and Biotechnology. vol. 31, No. 4 pp. 334-337 (1989).

Notification Concerning Transmittal of International Preliminary Report on Patentability (Chapter I of the Patent Cooperation Treaty) corresponding to International Patent Application No. PCT/US2010/041825 dated Jan. 26, 2012.

Notification of Transmittal of the International Search Report and the Written Opinion of the International Searching Authority, or the Declaration corresponding to International Patent Application No. PCT/US2010/041825 dated Sep. 1, 2010.

Pandya, B.A., and Snapper, M.L., "A Cross-Metathesis Route to the 5-$F_2$-Isoprostanes," J. Org. Chem. vol. 73, No. 10 pp. 3754-3758 (2008).

Shizuka, M., and Snapper, M.L., "Selective Synthesis of *ent*-15-*epi*-$F_{2t}$-Isoprostane and a Deuterated Derivative," Synthesis. vol. 15 pp. 2397-2403 (2007).

Taylor, "Organocopper Conjugate Addition-Enolate Trapping Reactions," Synthesis. pp. 364-392 (1985).

Wanasundara, U.N., and Shahidi, F., "Concentration of omega 3-polyunsaturated fatty acids of seal blubber oil by urea complexation: optimization of reaction conditions," Food Chemistry. vol. 65 pp. 41-49 (1999).

"Lubiprostone," Wikipedia, the free encyclopedia. 3 pages <http://en.wikipedia.org/wiki/Lubiprostone> (Accessed on Jan. 14, 2013).

* cited by examiner

SYNTHESIS OF PROSTANOIDS

CROSS REFERENCE TO RELATED APPLICATIONS

This application claims the benefit of U.S. Provisional Patent Application Ser. No. 61/225,047, filed Jul. 13, 2009, the disclosure of which is incorporated herein by reference in its entirety.

TECHNICAL FIELD

The presently disclosed subject matter relates to the synthesis of prostaglandins and prostaglandin analogs. The presently disclosed subject matter further relates to novel compounds that can be used in the synthesis of the prostaglandins and prostaglandin analogs and/or that can be used as prostaglandin prodrugs.

BACKGROUND

Prostaglandins are naturally occurring 20-carbon fatty acid derivatives produced by the oxidative metabolism of fatty acids (e.g., arachidonic acid). They and their non-naturally occurring analogs (which together can be referred to as prostanoids) have a wide variety of therapeutic uses.

Prostaglandins typically include at least one five-membered ring. For example, prostaglandin $F_{2\alpha}$ ($PGF_{2\alpha}$) and its analogs can comprise a cyclopentyl ring carrying two hydroxyl groups in a cis configuration and two side chains in a trans configuration. The side chains can contain double bonds and a variety of substituents.

Bimatoprost, an exemplary $PGF_\alpha$ prostaglandin analog, is sold in the U.S., Canada, and Europe by Allergan under the trade name LUMIGAN™ (Allergan, Inc., Irvine, Calif., United States of America) for use topically as eye drops to control the progression of glaucoma and in the management of ocular hypertension. It reduces intraocular pressure by increasing the outflow of aqueous fluid from the eyes. In December 2008, the U.S. Food and Drug Administration approved a cosmetic formulation of Bimatoprost, sold under the trade name LATISSE™ (Allergan, Inc., Irvine, Calif., United States of America) for use as a treatment for inadequate eyelash growth. It has further been suggested that Bimatoprost has the ability to reduce adipose (fat) tissue.

A variety of methods for synthesizing $PGF_\alpha$ and other prostaglandins and prostaglandin analogs are known. See e.g., International Publication No. WO 2005/058812 to Clissold et al., and the references cited therein. However, there remains a need in the art for additional methods of synthesizing prostanoids, such as but not limited to more versatile and efficient methods.

SUMMARY

The presently disclosed subject matter provides, in some embodiments, a compound of Formula (I):

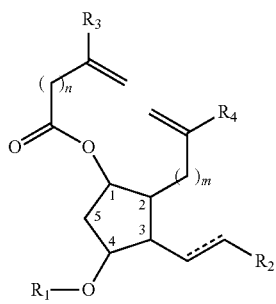

(I)

wherein: n and m are independently integers between 0 and 10; $R_1$ is H or a hydroxyl protecting group; $R_2$ is H, alkyl or aralkyl, optionally wherein the alkyl or aralkyl group further comprises one or more alkyl or aryl group substituents; and $R_3$ and $R_4$ are independently H, alkyl, aralkyl, or aryl, optionally wherein the alkyl, aralkyl, or aryl group further comprises one or more alkyl or aryl group substituents.

In some embodiments, the compound of Formula (I) is a compound of Formula (Ia) or (Ib):

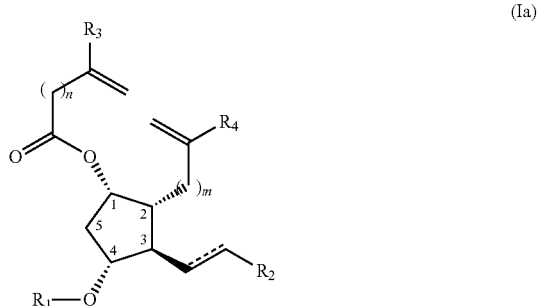

(Ia)

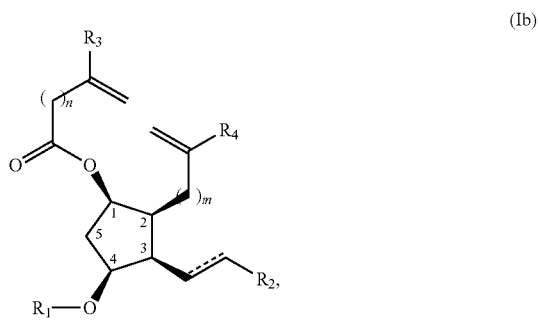

(Ib)

wherein: n and m are independently integers between 0 and 10; $R_1$ is H or a hydroxyl protecting group; $R_2$ is H, alkyl or aralkyl, optionally wherein the alkyl or aralkyl group further comprises one or more alkyl or aryl group substituents; and $R_3$ and $R_4$ are independently H, alkyl, aralkyl, or aryl, optionally wherein the alkyl, aralkyl, or aryl group further comprises one or more alkyl or aryl group substituents.

In some embodiments, $R_1$ is a silyl group. In some embodiments, $R_1$ is tert-butyldimethylsilyl.

In some embodiments, $R_2$ is alkyl or aralkyl, the alkyl or aralkyl group further comprising one or more substituents selected from the group consisting of carbonyl, halo, hydroxyl, protected hydroxyl, alkyl, alkoxyl, aryloxyl, $NH_2$, haloalkyl, alkylamino, arylamino, dialkylamino, and acylamino; or wherein two substitutents together form an alkylene group. In some embodiments, $R_2$ is a

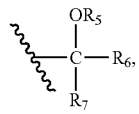

wherein: $R_5$ is H or a hydroxyl protecting group; $R_6$ is H or alkyl; and $R_7$ is selected from the group consisting of alkyl, $(CH_2)_q R_8$, and $(CH_2)_q OR_8$, wherein q is an integer from 0 to 4 and $R_8$ is alkyl optionally substituted with one or more alkyl group substituents or aryl optionally substituted with one or more aryl group substituents.

In some embodiments, $R_5$ is tert-butyldimethylsilyl and $R_6$ is H. In some embodiments, $R_7$ is selected from the group consisting of 2-phenylethyl, benzothienyl, and —CH$_2$—O—(C$_6$H$_4$—CF$_3$).

In some embodiments, n is 2 or 3. In some embodiments, m is 1.

In some embodiments, the compound is selected from the group consisting of:

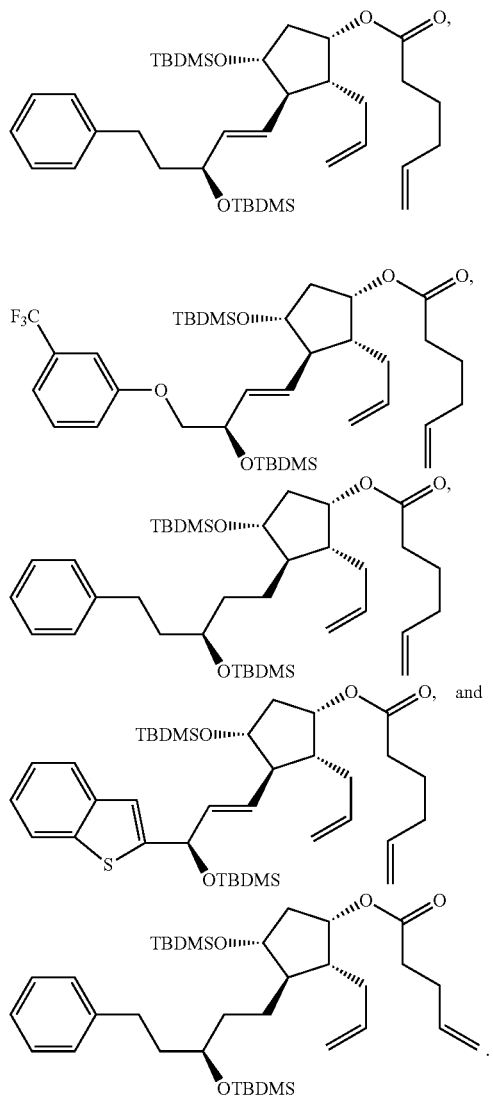

In some embodiments, the presently disclosed subject matter provides a compound of Formula (II):

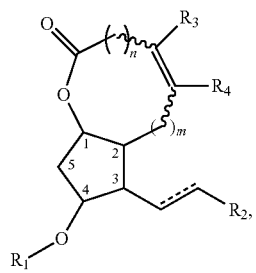

wherein: n and m are independently integers between 0 and 10; $R_1$ is H or a hydroxyl protecting group; $R_2$ is H, alkyl or aralkyl, optionally wherein the alkyl or aralkyl group further comprises one or more alkyl or aryl group substituents; and $R_3$ and $R_4$ are independently H, alkyl, aralkyl, or aryl, optionally wherein the alkyl, aralkyl, or aryl group further comprises one or more alkyl or aryl group substituents; wherein the compound of Formula (II) is selected from the group consisting of:

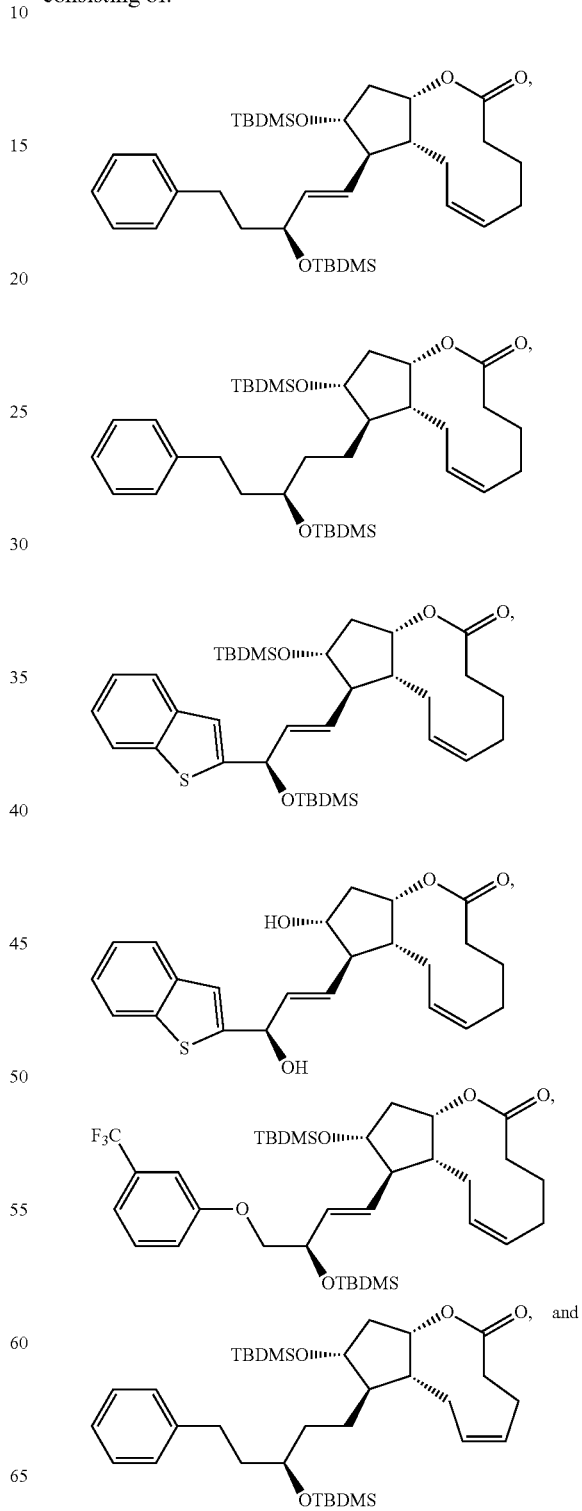

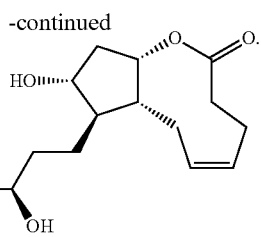

In some embodiments, the presently disclosed subject matter provides a pharmaceutical composition comprising a compound of Formula (II) and a pharmaceutically acceptable carrier. In some embodiments, the pharmaceutically acceptable carrier is pharmaceutically acceptable in humans.

In some embodiments, the presently disclosed subject matter provides a method of treating a disease or condition treatable by administration of a prostaglandin or prostaglandin analog, the method comprising administering to a subject in need of treatment thereof a compound selected from the group consisting of:

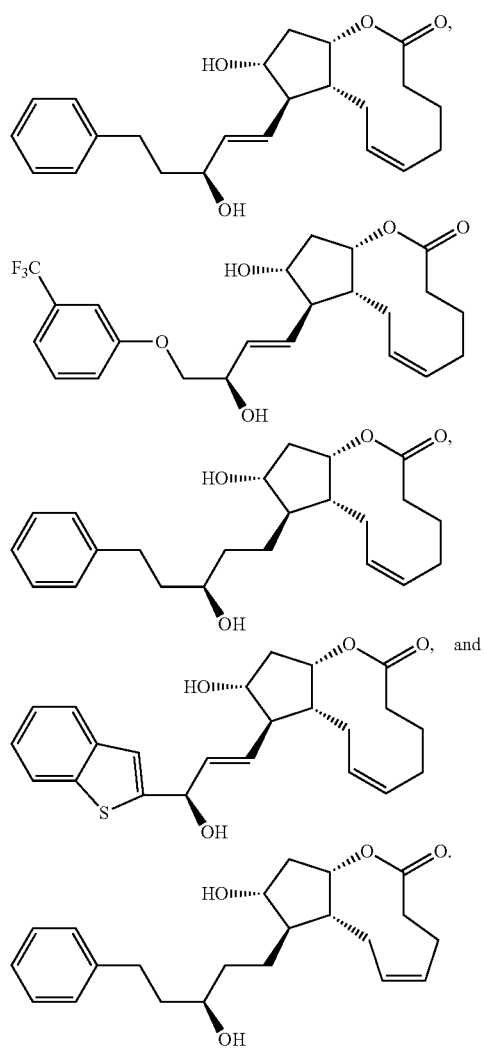

In some embodiments, the disease or condition is selected from the group consisting of glaucoma, ocular hypertension, pulmonary hypertension, inadequate eyelash/eyebrow growth, egg binding, ulcer, pain, fever and inflammation. In some embodiments, the disease or condition is treatable by inducing or accelerating labor.

In some embodiments, the presently disclosed subject matter provides a method of preparing a prostaglandin or prostaglandin analog, the method comprising: providing a compound of Formula (I):

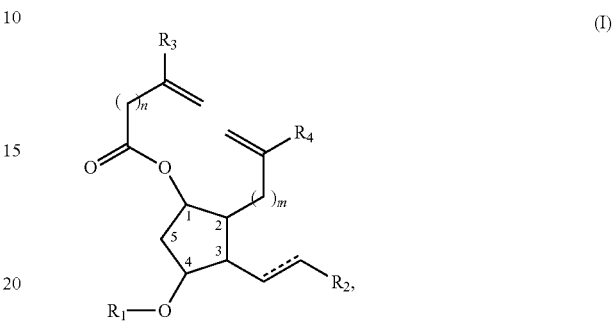

wherein: n and m are independently integers between 0 and 10; $R_1$ is H or a hydroxyl protecting group; $R_2$ is H, alkyl or aralkyl, optionally wherein the alkyl or aralkyl group further comprises one or more alkyl or aryl group substituents; and $R_3$ and $R_4$ are independently H, alkyl, aralkyl, or aryl, optionally wherein the alkyl, aralkyl, or aryl group further comprises one or more alkyl or aryl group substituents; reacting the compound of Formula (I) with a catalyst to perform a ring closing metathesis reaction, thereby forming a lactone; and reacting the lactone with a nucleophile, thereby forming a compound comprising a hydroxyl group and a carboxylic acid or derivative thereof.

In some embodiments, the catalyst is a transition metal carbene complex. In some embodiments, the catalyst is a ruthenium benyzlidene. In some embodiments, the catalyst is benzylidene-bis(tricyclohexylphosphine)dichlororuthenium.

In some embodiments, n+m=4.

In some embodiments, the ring closing metathesis reaction is performed in an aprotic solvent. In some embodiments, the aprotic solvent is dichloromethane.

In some embodiments, the nucleophile is selected from the group consisting of water, hydroxide, an alcohol, an alkoxide, an aryloxide, a thiol, a thiolate, an amine, an imide, and a sulfonamide, or a salt thereof. In some embodiments, the nucleophile is an alkylamine. In some embodiments, the alkylamine is ethylamine.

In some embodiments, reacting the lactone with a nucleophile is performed in an aprotic solvent. In some embodiments, the aprotic solvent is tetrahydrofuran (THF).

In some embodiments, the nucleophile is an alcohol, an alkoxide, an alkoxide salt, or a mixture thereof. In some embodiments, the nucleophile is 2-propanol, sodium 2-propoxide, or a mixture thereof.

In some embodiments, the method further comprises removing one or more hydroxyl protecting groups. In some embodiments, removing one or more hydroxyl protecting groups is performed prior to reacting the lactone with a nucleophile.

In some embodiments, the prostaglandin or prostaglandin analog is prostaglandin $F_{2\alpha}$ ($PGF_{2\alpha}$) or an analog thereof. In some embodiments, the prostaglandin or prostaglandin analog is selected from the group consisting of bimatoprost, latanoprost, travoprost, sulprostone, tafluprost, unoprostone, prostaglandin $F_{2\alpha}$ ($PGF_{2\alpha}$), carboprost, limaprost, fluprostenol, 13,14-dihydro-15-(2-benzothienyl)-15-pentanor $PGF_{1\alpha}$, and cloprostenol.

In some embodiments, the compound of Formula (I) is selected from the group consisting of:

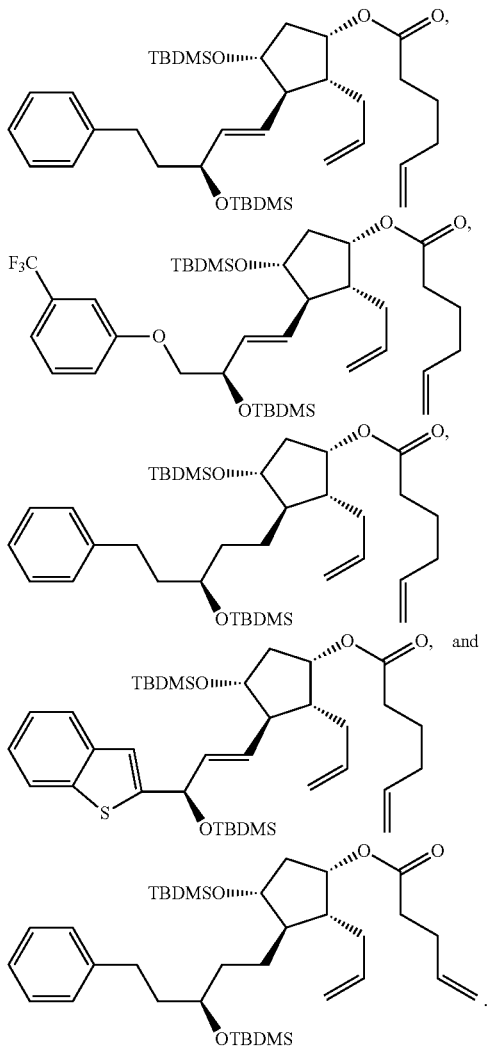

In some embodiments, the presently disclosed subject matter provides a prostaglanin or prostaglandin analog prepared by the method comprising: providing a compound of Formula (I); reacting the compound of Formula (I) with a catalyst to perform a ring closing metathesis reaction, thereby forming a lactone; and reacting the lactone with a nucleophile, thereby forming a compound comprising a hydroxyl group and a carboxylic acid or derivative thereof.

Accordingly, it is an object of the presently disclosed subject matter to provide compounds of Formula (I) and Formula (II) and to provide methods of synthesizing prostanoids.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

Following long-standing patent law convention, the terms "a", "an", and "the" refer to "one or more" when used in this application, including the claims. Thus, for example, reference to "a solvent" includes mixtures of one or more solvents, two or more solvents, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, molar equivalents, time, temperature, etc. is meant to encompass in one example variations of ±20% or ±10%, in another example ±5%, in another example ±1%, and in yet another example ±0.1% from the specified amount, as such variations are appropriate to perform the disclosed methods.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. "Comprising" is a term of art used in claim language, which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl, substituted alkyl (e.g., halo-substituted and perhalo-substituted alkyl, such as but not limited to, —$CF_3$), cycloalkyl, halo, nitro, hydroxyl, carbonyl, acyl, alkoxyl, aryloxyl, and aralkoxyl. Two alkyl group substituents can together form an alkylene group (e.g., an oxy or thio containing alkylene group, such as but not limited to methylenedioxy, ethylenedioxy, propylenedioxy, ethylenedithio, etc.).

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, and thiophenyl.

The aryl group can be optionally substituted (a "substituted aryl") with one or more aryl group substituents, which can be the same or different, wherein "aryl group substituent" includes alkyl, substituted alkyl (e.g., haloalkyl and perhaloalkyl, such as but not limited to —$CF_3$), cylcoalkyl, aryl, substituted aryl, aralkyl, halo, nitro, hydroxyl, acyl, alkoxyl, aryloxyl, and aralkyloxyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$O—). An alkylene group can have about 2 to about 3 carbon atoms and can further have 6-20 carbons.

The term "arylene" refers to a bivalent aromatic group.

As used herein, the term "acyl" refers to an organic carboxylic acid group wherein the —OH of the carboxylic acid group has been replaced with another substituent. Thus, the acyl group can be represented by RC(=O)—, wherein R is an alkyl, substituted alkyl, aralkyl, aryl or substituted aryl group as defined herein. As such, the term "acyl" specifically includes arylacyl groups, such as a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" refers to an alkyl —O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangeably with "alkoxyl".

"Aryloxyl" refers to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to an -aryl-alky or an -alkyl-aryl group wherein aryl and alkyl are as previously described, and included substituted aryl and substituted alkyl. Exemplary aralkyl groups include benzyl, phenylethyl, and naphthylmethyl.

"Aralkyloxyl" or "aralkoxyl" refer to an aralkyl-O— group wherein the aralkyl group is as previously described. An exemplary aralkyloxyl group is benzyloxyl.

The term "carbonyl" refers to the group —C(=O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The terms "halo", "halide", or "halogen" as used herein refer to fluoro, chloro, bromo, and iodo groups.

The term "sulfonyl" refers to the —$S(=O)_2R$ group, wherein R is alkyl, substituted alkyl, aralkyl, aryl, or substituted aryl.

The term "lactone" refers to a cyclic ester, wherein an oxygen and the carbonyl carbon atoms of the ester form part of the backbone of a heterocyclic group.

A dashed line representing a bond in a chemical formula indicates that the bond can be either present or absent. For example, the chemical structure:

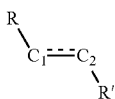

refers to compounds wherein $C_1$ and $C_2$ can be joined by either a single or double bond.

The term "nucleophile" refers to a molecule or ion that can form a bond with an electron deficient group (e.g., a carbonyl carbon) by donating one or two electrons. Nucleophiles include, but are not limited to, carbon, oxygen, and sulfur nucleophiles. Exemplary nucleophiles include, water, hydroxide, alcohols (i.e., aromatic and aliphatic alcohols), alkoxides, aryloxides (e.g., phenoxides), thiols (e.g, HS-alkyl, HS-aryl), thiolates (e.g., $^-$S-alkyl and $^-$S-aryl), sulfonamides, imides, and amines (e.g., ammonia, primary amines, and secondary amines). Nucleophiles can also be provided as salts, such as, but not limited to, alkali metal salts (i.e., salts comprising an anionic nucleophile, such as an alkoxide, aryloxide, or thiolate, and an alkali metal cation, such as but not limited to a sodium (Na), potassium (K), lithium (Li), rubidium (Rb), or cesium (Cs) cation.

The term "amine" refers to a molecule having the formula $N(R)_3$, or a protonated form thereof, wherein each R is independently H, alkyl, substituted alkyl, aryl, substituted aryl, or aralkyl or wherein two R groups together form an alkylene or arylene group. The term "primary amine" refers to an amine wherein at least two R groups are H. The term "secondary amine" refers to an amine wherein only one R group is H. The term "alkylamine" refers to an amine wherein two R groups are H and the other R group is alkyl or substituted alkyl. "Dialkylamine" refers to an amine where two R groups are alkyl. "Arylamine" refers to an amine wherein one R group is aryl. Amines can also be protonated, i.e., have the formula $[NH(R)_3]^+$.

The term "amino" refers to the group —$N(R)_2$ wherein each R is independently H, alkyl, substituted alkyl, aryl, substituted aryl, or aralkyl.

The term "hydroxyl protecting group" refers to groups that are known in the art of organic synthesis for masking hydroxyl groups during chemical group transformations elsewhere in the molecule. Accordingly, hydroxyl protecting groups are groups that can replace the hydrogen atom of a hydroxy group on a molecule and that are stable and non-reactive to reaction conditions to which the protected molecule is to be exposed. Suitable hydroxyl protecting groups are described, for example, in *Greene and Wuts*, Protective Groups in Organic Synthesis, 3$^{rd}$ Edition; New York, John Wiley & Sons, Inc., 1999. Hydroxyl protecting groups include, but are not limited to, groups that can be reacted with hydroxyl groups to form ethers, such as silyl ethers (e.g., trimethylsilyl (TMS), triethylsilyl (TES), tert-butyldimethylsilyl (TBDMS), t-butyldiphenylsilyl (TBDPS), or phenyldimethylsilyl ethers) substituted methyl ethers (e.g., methoxymethyl (MOM), benzyloxymethyl (BOM), tetrahydropyranyl (THP)), substituted ethyl ethers, benzyl ethers and substituted benzyl ethers; esters (e.g., acetate, formate, chloroacetate); and carbonates.

The term "silyl" refers to groups comprising silicon atoms (Si). In some embodiments, the term silyl refers to the group —$Si(R)_3$, wherein each R is independently alkyl, substituted alkyl, aralkyl, aryl, and substituted aryl. In some embodiments, the term silyl refers to a trialkylsilyl group.

As used herein, the terms "siloxy" and "silyl ether" refer to groups or compounds including a silicon-oxygen (Si—OR) bond and wherein R is an organic group, such as an alkyl or aryl group (i.e., methyl, ethyl, phenyl, etc.).

The term "aprotic solvent" refers to a solvent molecule which can neither accept nor donate a proton. Examples of aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide, N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

II. Compounds of Formula (I) and Formula (II)

The term "prostanoid" refers to prostaglandins and prostaglandin analogs. Prostaglandins are naturally occurring 20-carbon fatty acid derivatives produced biosynthetically by the oxidative metabolism of fatty acids (e.g., arachidonic acid). As used herein, the term "analog" is meant to refer to a biologically active, modified version of a natural product, wherein one or more atoms, such as but not limited to carbon, hydrogen, oxygen, nitrogen, sulfur or a halide, have been added or subtracted from the parent structure.

The structures of various known classes of prostaglandins are shown, for example, in U.S. Pat. No. 4,049,648; incorporated herein by reference. For instance, $PGF_\alpha$ and its analogs can comprise a cyclopentyl ring carrying two hydroxyl groups in a cis configuration and two side chains in a trans configuration. The side chains can contain double bonds and a variety of substituents.

The presently disclosed subject matter provides, in one aspect, novel compounds that can be used, for example, as prodrugs for prostaglandins or prostaglandin analogs and/or as synthetic intermediates in the synthesis of a wide variety of prostaglandins (e.g., $PGE_2$, $PGE_3$, dihydro-$PGE_1$, $PGF_{2\alpha}$, $PGF_{3\alpha}$, dihydro-$PGF_{1\alpha}$, and the like) and prostaglandin analogs. In some embodiments, the compounds can be used as synthetic intermediates and/or prodrugs for a prostaglandin or prostaglandin analog such as, but not limited to, Bimatoprost, Latanoprost, Travoprost, Sulprostone, Tafluprost, Unoprostone, Prostaglandin $F_{2\alpha}$ ($PGF_{2\alpha}$, also known as Dinoprost), Carboprost, Limaprost, Fluprostenol, 13,14-dihydro-15-(2-benzothienyl)-15-pentanor $PGF_{1\alpha}$, and Cloprostenol.

II.A. Compounds of Formula (I)

In some embodiments, the presently disclosed subject matter provides a compound of Formula (I):

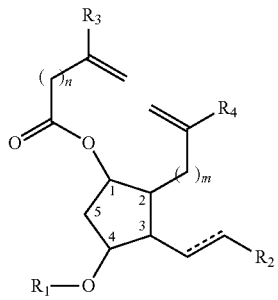
(I)

wherein:
n and m are independently integers between 0 and 10;
$R_1$ is H or a hydroxyl protecting group;
$R_2$ is selected from the group including, but not limited to, H, alkyl and aralkyl, optionally wherein the alkyl or aralkyl group further comprises one or more alkyl or aryl group substituents; and
$R_3$ and $R_4$ are independently selected from the group including, but not limited to, H, alkyl, aralkyl, and aryl, optionally wherein the alkyl, aralkyl, or aryl group further comprises one or more alkyl or aryl group substituents.

In some embodiments, the substituents at carbon 1 and carbon 2 are oriented cis to one another. In some embodiments, the substituents at carbon 3 and carbon 4 are oriented trans to one another. Thus, in some embodiments, the compound of Formula (I) is a compound of Formula (Ia) or (Ib):

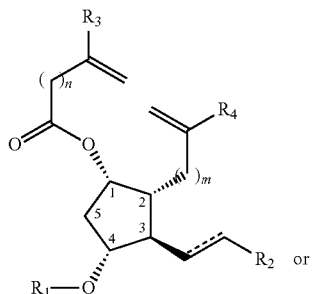
(Ia)

or

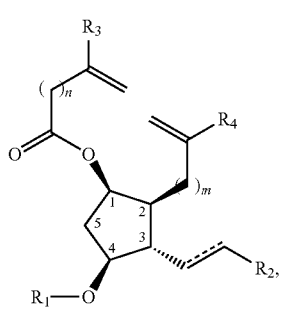
(Ib)

wherein:
n and m are independently integers between 0 and 10;
$R_1$ is H or a hydroxyl protecting group;
$R_2$ is selected from the group including, but not limited to, H, alkyl and aralkyl, optionally wherein the alkyl or aralkyl group further comprises one or more alkyl or aryl group substituents; and
$R_3$ and $R_4$ are independently selected from the group including, but not limited to, H, alkyl, aralkyl, and aryl, optionally wherein the alkyl, aralkyl, or aryl group further comprises one or more alkyl or aryl group substituents.

$R_1$ can be any suitable hydroxyl protecting group. For example, suitable hydroxyl protecting groups include, but are not limited to silyl protecting groups (e.g., TMS, TES, TBDMS, TBDPS, and phenyldimethylsilyl); substituted methyl ethers (e.g., MOM, BOM, and THP); substituted ethyl ethers; benzyl ethers and substituted benzyl ethers; esters (e.g., acetate, formate, chloroacetate); and carbonates. In some embodiments, $R_1$ is a silyl group (e.g., TMS, TES, TBDMS, TBDPS and the like), such that the molecule of Formula (I), (Ia), or (Ib) includes a silyl ether. In some embodiments, $R_1$ is TBDMS.

In some embodiments, $R_2$ is alkyl or aralkyl, wherein the alkyl or aralkyl group comprises a branched alkyl group and/or one or more alkyl and/or aryl group substituents selected from the group including, but not limited to, carbonyl, halo, hydroxyl, protected hydroxyl, alkyl, alkoxyl, aryloxyl, and amino (e.g., —$NH_2$, protected amino, alkylamino, dialkylamino, arylamino, acylamino or another functionalized amino group). In some embodiments, $R_2$ can be substituted by two alkyl group substituents which together form an alkylene group (e.g., an ethylenedioxy, propylenedioxy, or ethylenedithio group).

In some embodiments, $R_2$ is a group of the formula:

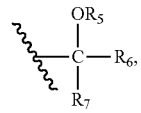

wherein $R_5$ is H or a hydroxyl protecting group; $R_6$ is H or alkyl; and $R_7$ is selected from the group including, but not limited to, alkyl (e.g., branched or straight chain alkyl), $(CH_2)_q R_8$, and $(CH_2)_q OR_8$, wherein q is an integer from 0 to 4 (i.e., 0, 1, 2, 3, or 4) and $R_8$ is alkyl optionally substituted with one or more alkyl group substituents or aryl optionally substituted with one or more aryl group substituents (e.g., halo, alkyl, substituted alkyl (e.g., haloalkyl)). In some embodiments, the aryl group of $R_8$ is phenyl or substituted phenyl. In some embodiments, the aryl group of $R_8$ is heteroaryl (e.g., benzothienyl).

$R_5$ can be any suitable hydroxyl protecting group, and can be the same or different as any hydroxyl protecting group at $R_1$. For example, suitable hydroxyl protecting groups include, but are not limited to silyl protecting groups (e.g., TMS, TES, TBDMS, TBDPS, and phenyldimethylsilyl); substituted methyl ethers (e.g., MOM, BOM, and THP); substituted ethyl ethers; benzyl ethers and substituted benzyl ethers; esters (e.g., acetate, formate, chloroacetate); and carbonates. In some embodiments, $R_1$ and $R_5$ are the same hydroxyl protecting group or are both silyl protecting groups.

In some embodiments, the compound of Formula (I) comprises one or more unprotected hydroxyl groups. Thus, in some embodiments, $R_1$ and/or $R_5$ are H.

In some embodiments, $R_5$ is tert-butyldimethylsilyl and $R_6$ is H or methyl. In some embodiments, $R_7$ is selected from the group comprising 2-phenylethyl, benzothienyl, pentyl, (2-methyl)hexyl, —CH$_2$—O-phenyl, —CH$_2$—O-phenyl-Cl, and —CH$_2$—O-phenyl-CF$_3$.

In some embodiments, R$_2$ is —CF$_2$CH$_2$O-phenyl or

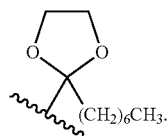

In some embodiments, one or both of R$_3$ and R$_4$ is straight chain, branched, or substituted alkyl. In some embodiments, R$_3$ and/or R$_4$ are H.

The variable n can be any integer between 0 and 10 (i.e., 0, 1, 2, 3, 4, 5, 6, 7, 8, 9, or 10). In some embodiments, n is 2 or 3. In some embodiments, n is 0.

The variable m can be any integer between 0 and 10 (i.e., 0, 1, 2, 3, 4, 5, 6, 7, 8, 9, or 10). In some embodiments, m is 1. In some embodiments, m is 4.

The sum of variables n and m can be any integer between 0 and 20 (i.e., n+m can be 0, 1, 2, 3, 4, 5, 6, 7, 8, 9, 10, 11, 12, 13, 14, 15, 16, 17, 18, 19, or 20). In some embodiments, n+m=3 or 4.

In some embodiments, the compound of Formula (I) is selected from the group comprising:

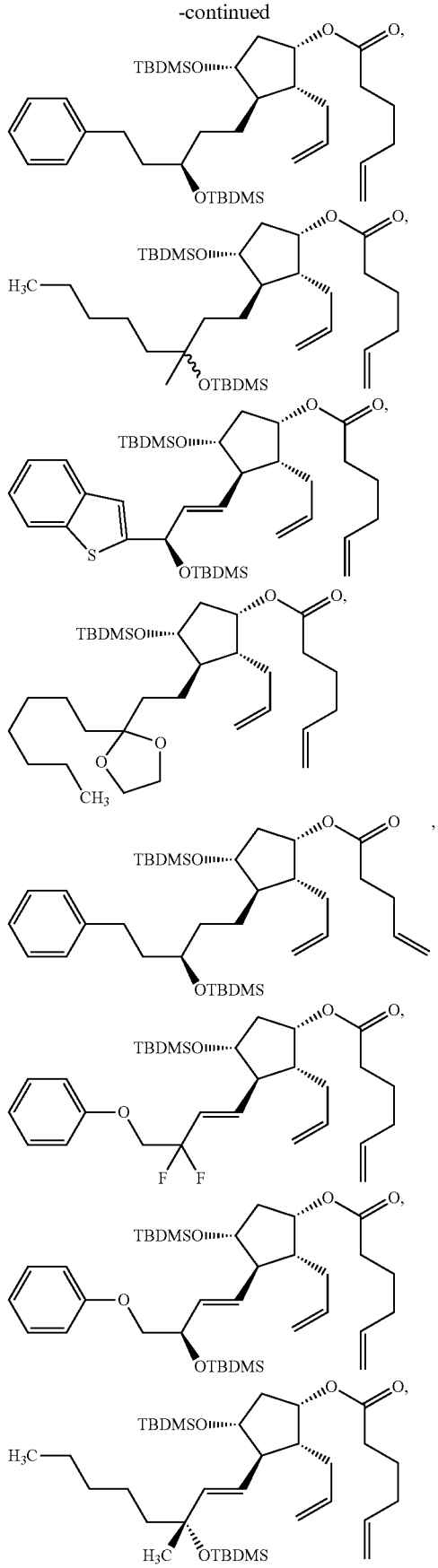

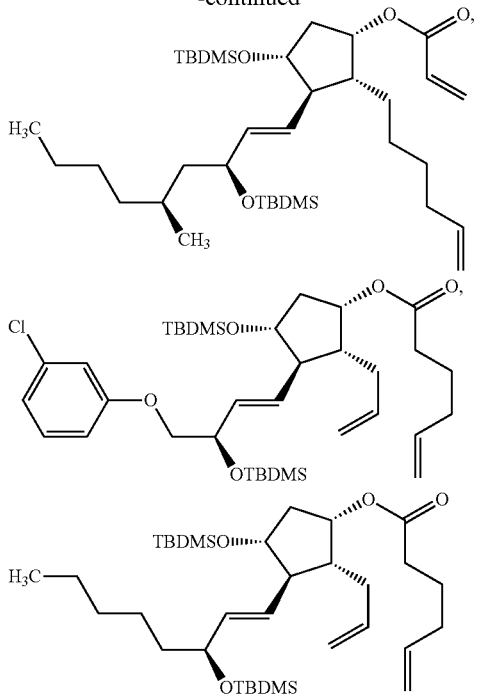

or the corresponding unprotected compound thereof (i.e., the corresponding compound of Formula (I) wherein the —OTBDMS groups are OH groups).

II.B. Compounds of Formula (II).

In some embodiments, the presently disclosed subject matter provides a cyclopentane derivative comprising a lactone. In some embodiments, the presently disclosed subject matter provides a compound of Formula (II):

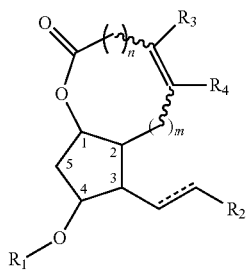

wherein:
n and m are independently integers between 0 and 10;
$R_1$ is H or a hydroxyl protecting group;
$R_2$ is selected from the group including, but not limited to, H, alkyl and aralkyl, optionally wherein the alkyl or aralkyl group further comprises one or more alkyl or aryl group substituents; and
$R_3$ and $R_4$ are independently selected from the group including, but not limited to, H, alkyl, aralkyl, and aryl, optionally wherein the alkyl, aralkyl, or aryl group further comprises one or more alkyl or aryl group substituents.

In some embodiments, the substituents at carbon 1 and carbon 2 are oriented cis to one another. In some embodiments, the substituents at carbon 3 and carbon 4 are oriented trans to one another. Thus, in some embodiments, the compound of Formula (II) is a compound of Formula (IIa) or (IIb):

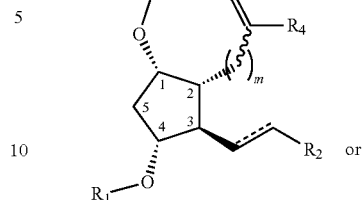

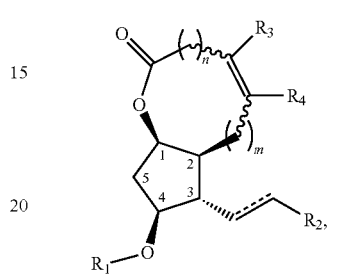

wherein:
n and m are independently integers between 0 and 10;
$R_1$ is H or a hydroxyl protecting group;
$R_2$ is selected from the group including, but not limited to, H, alkyl and aralkyl, optionally wherein the alkyl or aralkyl group further comprises one or more alkyl or aryl group substituents; and
$R_3$ and $R_4$ are independently selected from the group including, but not limited to, H, alkyl, aralkyl, and aryl, optionally wherein the alkyl, aralkyl, or aryl group further comprises one or more alkyl or aryl group substituents.

$R_1$ can be any suitable hydroxyl protecting group. For example, suitable hydroxyl protecting groups include, but are not limited to silyl protecting groups (e.g., TMS, TES, TBDMS, TBDPS, and phenyldimethylsilyl); substituted methyl ethers (e.g., MOM, BOM, and THP); substituted ethyl ethers; benzyl ethers and substituted benzyl ethers; esters (e.g., acetate, formate, chloroacetate); and carbonates. In some embodiments, $R_1$ is a silyl group (e.g., TMS, TES, TBDMS, TBDPS and the like), such that the molecule of Formula (II), (IIa), or (IIb) includes a silyl ether. In some embodiments, $R_1$ is TBDMS.

In some embodiments, $R_2$ is alkyl or aralkyl, wherein the alkyl or aralkyl group further comprises a branched alkyl group and/or one or more alkyl and/or aryl group substituents selected from, but not limited to, carbonyl, halo, hydroxyl, protected hydroxyl, alkyl, alkoxyl, aryloxyl, and amino (e.g., —NH$_2$, protected amino, alkylamino, dialkylamino, arylamino, acylamino or another functionalized amino group). In some embodiments, $R_2$ can be substituted by two alkyl group substituents which together form an alkylene group (e.g., an ethylenedioxy, propylenedioxy, or ethylenedithio group).

In some embodiments, $R_2$ is a group of the formula:

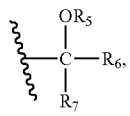

wherein $R_5$ is H or a hydroxyl protecting group; $R_6$ is H or alkyl; and $R_7$ is selected from the group including, but not limited to, alkyl (e.g., branched or straight chain alkyl), $(CH_2)_q R_8$, and $(CH_2)_q OR_8$, wherein q is an integer from 0 to 4 (i.e., 0, 1, 2, 3, or 4) and $R_8$ is alkyl optionally substituted with one or more alkyl group substituents or aryl, optionally substituted with one or more aryl group substituents (e.g., halo, alkyl, substituted alkyl (e.g., haloalkyl)). In some embodiments, the aryl group of $R_8$ is phenyl or substituted phenyl. In some embodiments, the aryl group of $R_8$ can be heteroaryl (e.g., benzothienyl).

$R_5$ can be any suitable hydroxyl protecting group, and can be the same or different as any hydroxyl protecting group at $R_1$. For example, suitable hydroxyl protecting groups include, but are not limited to silyl protecting groups (e.g., TMS, TES, TBDMS, TBDPS, and phenyldimethylsilyl); substituted methyl ethers (e.g., MOM, BOM, and THP); substituted ethyl ethers; benzyl ethers and substituted benzyl ethers; esters (e.g., acetate, formate, chloroacetate); and carbonates. In some embodiments, $R_1$ and $R_5$ are the same hydroxyl protecting group or are both silyl protecting groups.

In some embodiments, the compound of Formula (II) does not comprise protecting groups and $R_1$ and $R_5$ are each H.

In some embodiments, $R_5$ is tert-butyldimethylsilyl and $R_6$ is H or methyl. In some embodiments, $R_7$ is selected from the group comprising 2-phenylethyl, benzothienyl, pentyl, (2-methyl)hexyl, —CH$_2$—O-phenyl, —CH$_2$—O-phenyl-Cl, and —CH$_2$—O-phenyl-CF$_3$.

In some embodiments, $R_2$ is —CF$_2$CH$_2$O-phenyl or

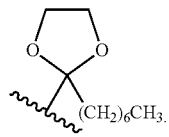

In some embodiments, one or both of $R_3$ and $R_4$ are straight chain, branched, or substituted alkyl. In some embodiments, $R_3$ and/or $R_4$ are H.

The variable n can be any integer between 0 and 10 (i.e., 0, 1, 2, 3, 4, 5, 6, 7, 8, 9, or 10). In some embodiments, n is 2 or 3. In some embodiments, n is 0.

The variable m can be any integer between 0 and 10 (i.e., 0, 1, 2, 3, 4, 5, 6, 7, 8, 9, or 10). In some embodiments, m is between 1 and 10. In some embodiments, m is 1. In some embodiments, m is 4.

The sum of variables n and m can be any integer between 0 and 20 (i.e., n+m can be 0, 1, 2, 3, 4, 5, 6, 7, 8, 9, 10, 11, 12, 13, 14, 15, 16, 17, 18, 19, or 20). In some embodiments, n+m=3 or 4 and the lactone of Formula (II) is a nine- or ten-membered ring.

The double bond of the lactone ring of the compounds of Formula (II), (IIa), or (IIb) can be cis or trans with regard to the orientation of the substituents that form the ring (i.e., the substituents that include the —(CH$_2$)$_n$— and —(CH$_2$)$_m$— groups). When the lactone ring is smaller (e.g., m+n is 4 or less), the double bond substituents that are part of the ring can be on the same side of the double bond in order to reduce ring strain. Thus, in some embodiments, wherein m+n is 4 or less, the double bond of the lactone is cis. When the lactone ring is larger, the double bond can be cis or trans with regard to the orientation of the substituents that form the ring. Thus, in some embodiments, wherein m+n is greater than 4, the double bond is trans. In some embodiments, wherein m+n is greater than 4, the double bond is cis.

In some embodiments, the compounds of Formula (II) are selected from the group comprising:

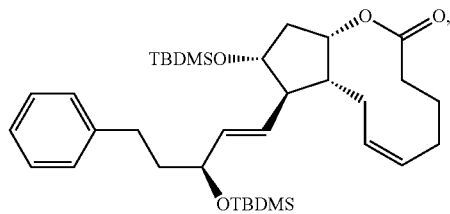

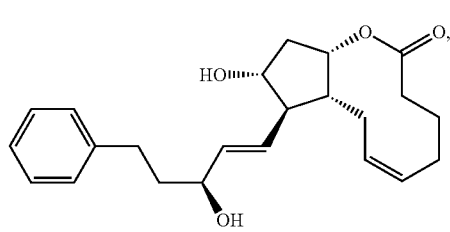

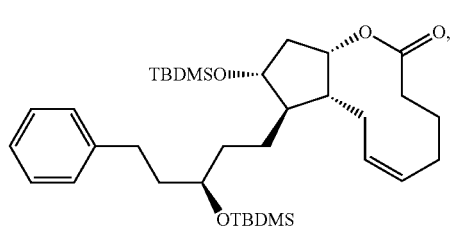

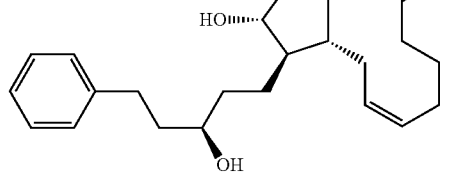

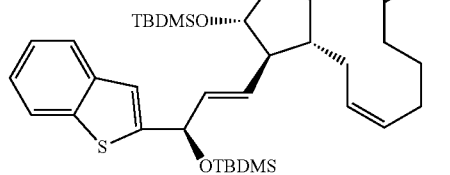

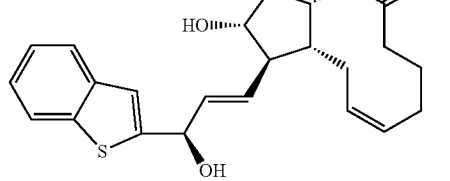

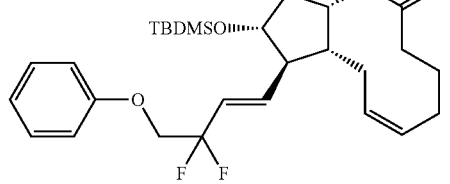

-continued
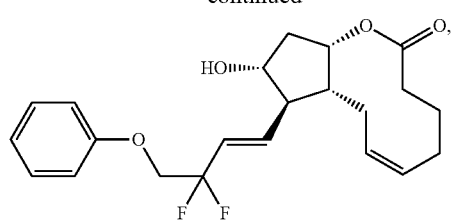
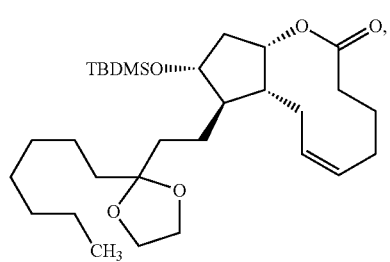
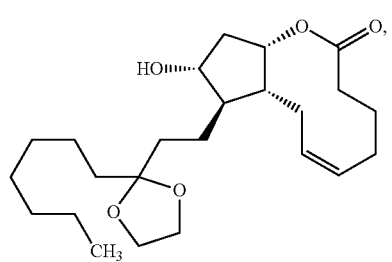
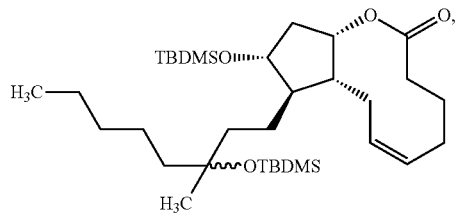
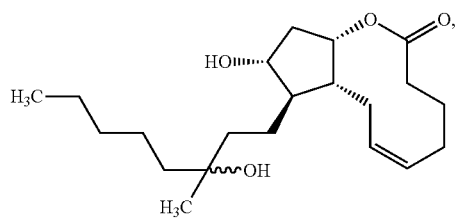
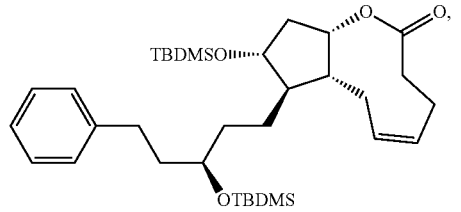
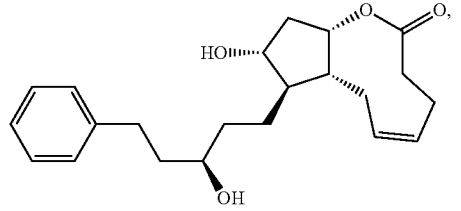
-continued
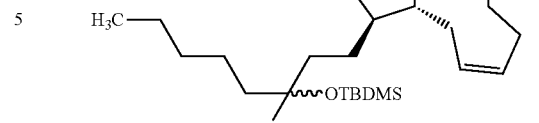
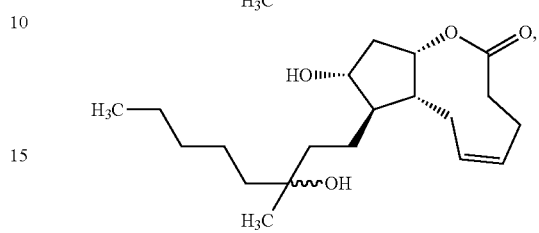
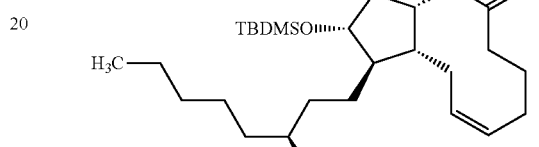
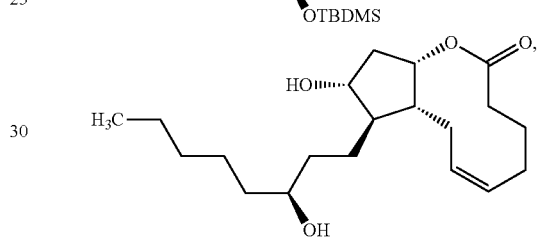
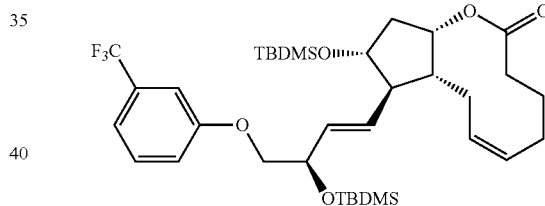
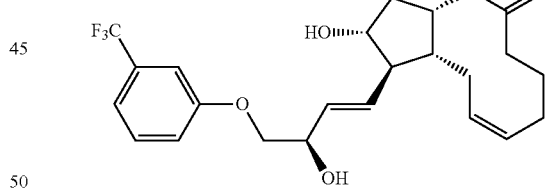
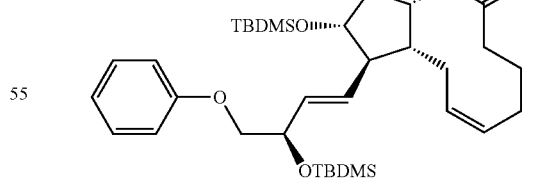
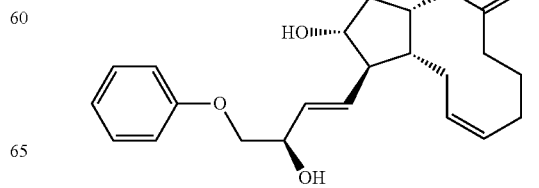

-continued

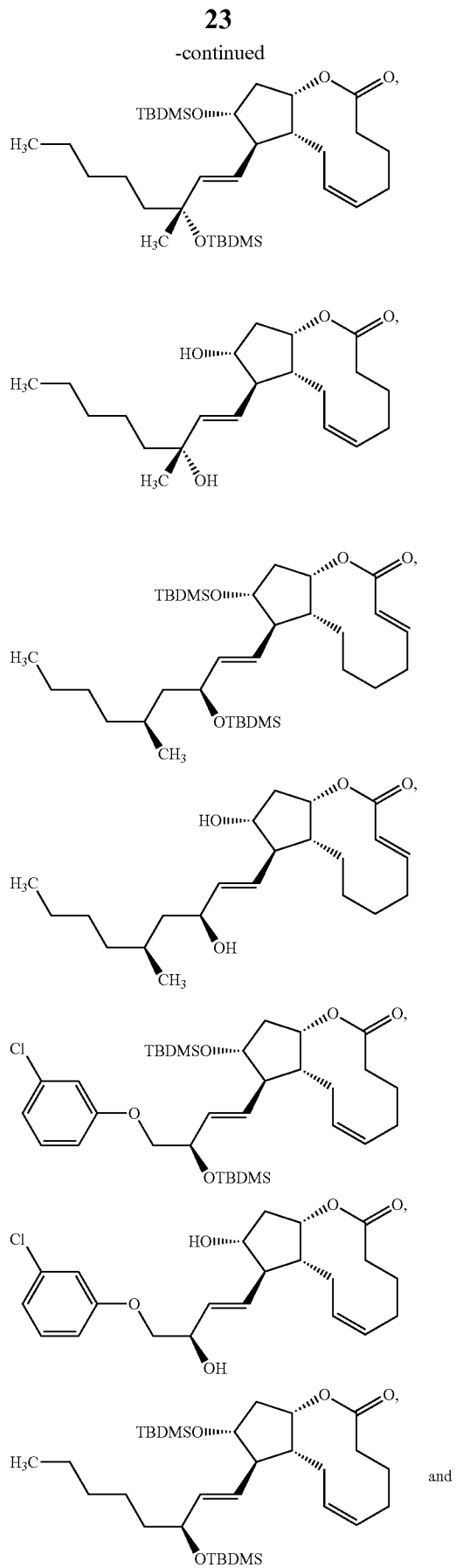

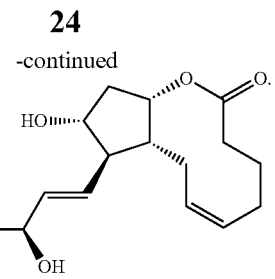

III. Methods of Preparing Compounds of Formula (I) and Formula (II) and Methods of Preparing Prostanoids A variety of approaches and methods for synthesizing prostaglandins and prostaglandin analogs have been previously described. See, e.g., Collins and Djuric, *Chem. Rev.*, 93, 1533-1564 (1993). The presently disclosed prostanoid synthesis (shown in Schemes 1 and 2, below), can use as an α-substituted hydroxycyclopentenone as a starting material. See for example compound 1 in Scheme 1. Prior uses and methods of preparing α-substituted chiral hydroxycyclopentenones have been previously reported. See Mitsuda et al., *Applied Microbiology and Biotechnology*, 31(4), 334-337 (1989); Hazato et al., *Chem. Pharm. Bull.*, 33(5), 1815-1825 (1985); and U.S. Pat. No. 7,109,371; each of which is incorporated herein by reference in its entirety.

In accordance with the presently disclosed subject matter, compounds of Formula (I) (e.g., compounds of Formula (Ia) or (Ib)) can be prepared as shown in Scheme 1 below. As shown in Scheme 1, intermediate 3 can be prepared by the 1,4-conjugate addition of a reagent formed, for example, from alkene reagent 2, alkyne reagent 2', or alkyl halide 2" and cyclopentenone 1. Suitable alkene compounds for preparing reagents for these conjugate additions, include, but are not limited to, vinyl halides and vinyl ethers. Stereoselective conjugate addition of organometallic reagents to α,β-unsaturated ketones has been previously described. See, e.g., Taylor, *Synthesis*, 364-392 (1985), incorporated herein by reference in its entirety.

The ketone of intermediate 3 can then be reduced to provide alcohol 4. Any suitable reducing agent can be used. For example, the reducing agent can be a boron or aluminum hydride donor, such as, but not limited to sodium borohydride ($NaBH_4$), lithium aluminum hydride ($LiAlH_4$), and diisobutylaluminum hydride (DIBALH). Reduction of ketone 3 can be non-stereoselective, leading to a mixture of isomeric alcohols or stereoselective, leading to the formation of a single isomer of alcohol 4, depending upon the reducing agent and/or conditions used. In some embodiments, the reducing agent can be a stereoselective reducing agent. Exemplary stereoselective reducing agents include, for example, those available under that trademark SELECTRIDE™ (Sigma-Aldrich, St. Louis, Mo., United States of America).

Alcohol 4 (either as a single isomer or as a mixture of isomers) can be esterified (e.g., using a suitable carbodiimide and non-nucleophilic base) with an alkenoic acid (such as but not limited to, 2-propenoic acid (i.e., acrylic acid), 2-methyl-2-propenoic acid (i.e., methacrylic acid), 2-butenoic acid (i.e., crotonic acid), 3-butenoic acid, 4-pentenoic acid, 5-hexenoic acid, 6-heptenoic acid, 7-octenoic acid, 8-nonenoic acid, 9-decenoic acid, 10-undecenoic acid, 11-dodecenoic acid, and 12-tridecenoic acid) or a derivative thereof (e.g., an acid chloride, activated ester (e.g, a pentafluorophenyl ester), or anhydride) to provide a compound of Formula (I).

Any suitable solvent can be used for these reactions. In some embodiments, suitable solvents for these reactions include aprotic solvents, such as, but not limited to, ethers (e.g., tetrahydrofuran (THF) or methyl tert-butyl ether (MTBE)) or halogenated alkanes (e.g., dichloromethane (DCM)).

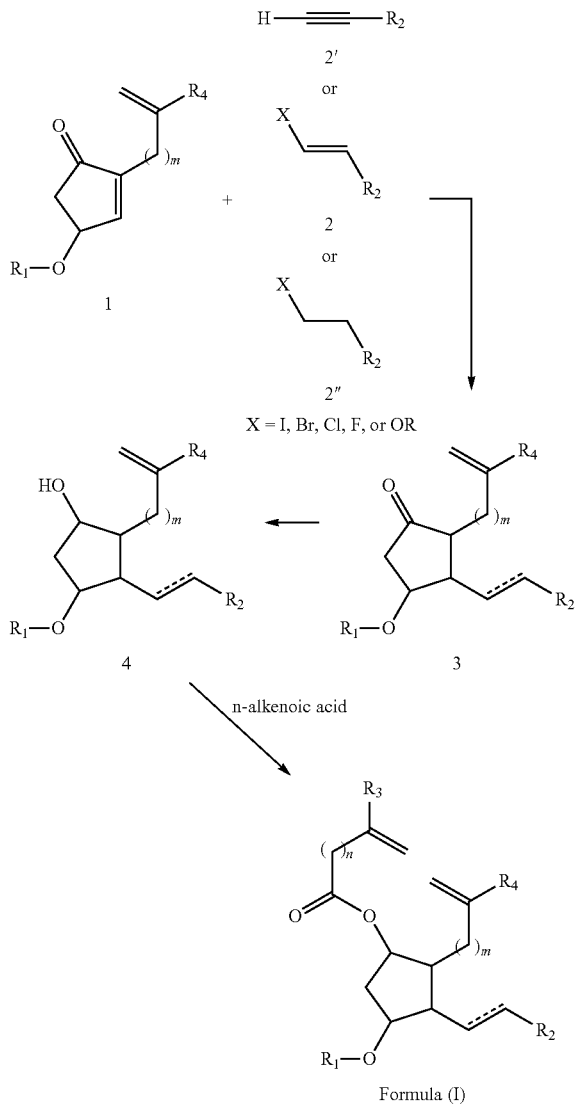

Scheme 1. Synthesis of Compounds of Formula (I).

Compounds of Formula (I) can be used to synthesize compounds of Formula (II) (e.g., compound of Formula (IIa) or (IIb)) and/or prostaglandins or analogs thereof as shown in Scheme 2, wherein a compound of Formula (I) undergoes ring-closing metathesis catalyzed by a transition metal catalyst, such as, but not limited to a ruthenium-based catalyst. To drive the reaction to completion, ethylene formed as a side product during the ring-closing reaction can be removed from the reaction system. If the compound of Formula (I) includes one or more protecting groups (e.g., hydroxyl protecting groups), these can be removed prior to the ring-closing metathesis reaction, or, alternatively, the compound of Formula (I) can be subjected to ring-closing metathesis in protected form.

The lactone formed from the metathesis (i.e., a compound of Formula (II)) can then be reacted with a nucleophile (e.g., water, hydroxide, alcohol, alkoxide, aryloxide, thiol, alkylthiolate, arylthiolate, amine, sulfonamide, imide, or a salt thereof) to open the lactone to provide protected ring-opened compound 5, which includes a hydroxyl group on the cyclopentane ring and a carboxylic acid or carboxylic acid derivative. If necessary, protecting groups can then be removed, and/or the newly formed hydroxyl group can be oxidized to the ketone and then protecting groups can be removed, and/or carbon-carbon double bonds can be reduced to carbon-carbon single bonds (e.g., via catalytic hydrogenation). Alternatively, the protecting groups of the compound of Formula (II) can be removed prior to the lactone ring opening (to form an unprotected compound of Formula (II)). Regardless of the order of the ring opening and any deprotection steps, the carboxylic acid or derivative thereof that results from the ring opening reaction can also be further elaborated as desired. For example, the carboxylic acid or derivative thereof can be reduced or partially reduced to form an aldehyde or alcohol group; hydrolyzed (e.g., an ester or amide can be transformed into a carboxylic acid or carboxylate), or transformed into a different type of carboxylic acid derivative. For example, a carboxylic acid group can be synthetically transformed into an acid chloride, anhydride, ester or amide, and an ester can be transformed into an amide.

Scheme 2. Synthesis of Compounds of Formula (II) and Prostanoids.

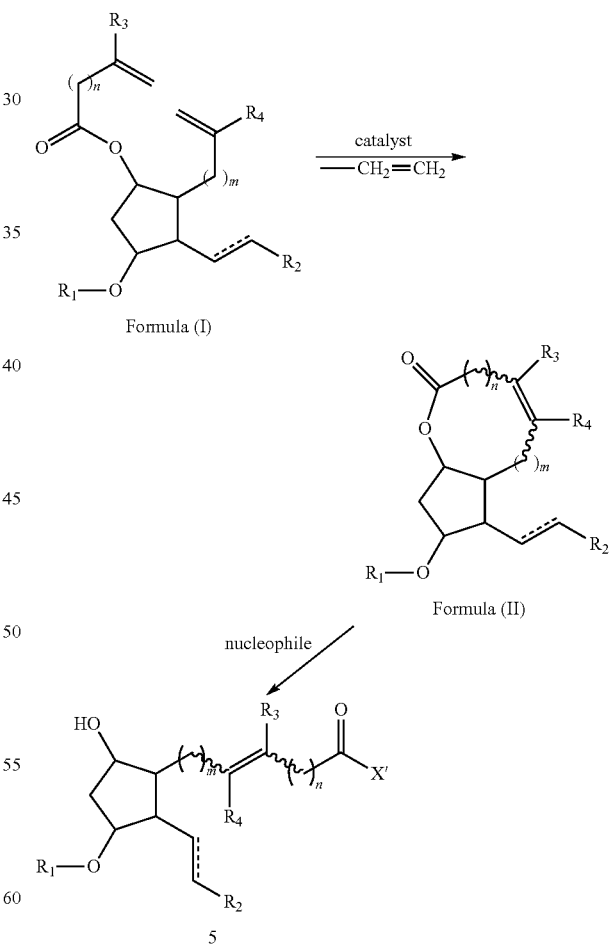

X' = OH, O-Alkyl, O-Aryl, NH$_2$, NH-Alkyl, NH-Aryl, NH-Sulfonyl-Alkyl, NH-Sulfonyl-Aryl Accordingly, in some embodiments, the presently disclosed subject matter provides a process for preparing prostaglandins and prostaglandin analogs using an approach based upon ring-closing metathesis (RCM) to form prostaglanin-1,9-lactones. Ring-closing alkyne metathesis to form prostaglandin-1,15-lactones has been previously described. See Fürstner et al., *J. Am. Chem. Soc.*, 122, 11799-11805 (2000). In addition, Pandya and Snapper have previously described syntheses of 5-F2-isoprostanes that can proceed via either ring-opening cross-metathesis (ROCM) of a bicyclo [3.2.0]heptene and another olefin or via ring-opening/ring-closing metathesis (RO/RCM) of bicyclo[3.2.0]heptenes comprising alkene-containing side chains. See Pandya and Snapper, *J. Org. Chem.*, 73(10), 3754-3758 (2008).

The presently disclosed synthetic route is both highly versatile and scalable and uses readily available or easily prepared starting materials. Each of the individual steps in the synthesis can be performed in good yield. For example, the lactones of Formula (II) can be routinely prepared from the compounds of Formula (I) by RCM in 60, 65, 70, 75, 80, or 85% or greater yield, leading to good overall yields of the prostaglandin or analog thereof.

In some embodiments, the process for preparing the prostaglandin or prostaglandin analog comprises:

providing a compound of Formula (I):

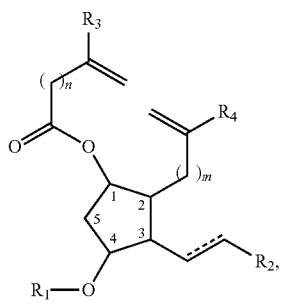

(I)

wherein:

n and m are independently integers between 0 and 10;

$R_1$ is H or a hydroxyl protecting group;

$R_2$ is selected from the group including, but not limited to, H, alkyl and aralkyl, optionally wherein the alkyl or aralkyl group further comprises one or more alkyl or aryl group substituents; and $R_3$ and $R_4$ are independently selected from the group including, but not limited to, H, alkyl, aralkyl, and aryl, optionally wherein the alkyl, aralkyl, or aryl group further comprises one or more alkyl or aryl group substituents;

reacting the compound of Formula (I) with a catalyst to perform a ring closing metathesis reaction, thereby forming a lactone; and reacting the lactone with a nucleophile, thereby forming a compound (i.e., a prostaglandin or prostaglandin analog) comprising a hydroxyl group and a carboxylic acid or derivative thereof (e.g., an amide (e.g., a primary amide, alkyl-substituted amide, aralkyl-substituted amide, sulfonyl-substituted amide, aralkyl-substituted amide, aryl-substituted amide, or di-substituted (e.g., dialkyl, diaryl or N-alkyl-N-aryl) amide, ester, or anhydride).

In some embodiments, the catalyst comprises a transition metal such as, but not limited to, Ni, W, Ru, Rh, or Mo. In some embodiments, the transition metal is Ru. In some embodiments, the catalyst is a transition metal carbene complex, such as, but not limited to a transition metal benzylidene. In some embodiments, the catalyst is a Schrock, Grubbs, or Hoveyda-Grubbs catalyst. In some embodiments, the catalyst is benzylidene-bis(tricyclohexylphosphine) dichlororuthenium.

In some embodiments, the compound of Formula (I) is a compound of Formula (Ia) or Formula (Ib). In some embodiments, the lactone is a compound of Formula (II) (e.g., a compound of Formula (IIa) or (IIb)). In some embodiments, the lactone is a nine-membered or ten-membered ring and n+m is 3 or 4. In some embodiments, the lactone is a ten-membered ring and n+m is 4. In some embodiments, n is 2 or 3 and m is 1. In some embodiments, n is 3 and m is 1. In some embodiments, n is 0 and m is 4.

In some embodiments, reacting the compound of Formula (I) with a catalyst to perform a ring closing metathesis reaction is performed in a non-polar, aprotic solvent, such as, but not limited to, dichloromethane.

In some embodiments, the nucleophile is selected from the group comprising water, alcohol (e.g., an aliphatic or aromatic alcohol), a thiol (e.g., alkylthiols and arylthiols), and amine (or another nitrogen nucleophile, such as, but not limited to a sulfonamide or imide). The nucleophiles can be provided in a deprotonated form (e.g., as hydroxide, an alkoxide or a thiolate) or as salts, such as salts of alkali metal cations (e.g., sodium, lithium, potassium, or cesium salts of hydroxide, an alkoxide or a thiolate) or deprotonated in situ during a reaction. In some embodiments, the nucleophile is an alkylamine or arylamine, such as, but not limited to, ethylamine. In some embodiments, the nucleophile is an alcohol, an alkoxide, an alkoxide salt, or a mixture thereof, such as, but not limited to 2-propanol and/or sodium isopropoxide.

When the nucleophile is an amine, ring opening can provide a compound comprising an amide. When the nucleophile is an alcohol, alkoxide or aryloxide, ring opening can provide a compound comprising an ester. When the nucleophile is water or hydroxide, ring opening can provide a carboxylic acid, which can be further reacted, if desired, to provide an ester or other carboxylic acid derivative.

In some embodiments, reacting the lactone with a nucleophile is performed in an aprotic solvent, such as, but not limited to, tetrahydrofuran. In some embodiments, ring opening is performed in a protic solvent, such as an alcohol.

If desired, the ring-opened product can be further reacted to oxidize the hydroxyl group formed from opening the lactone (e.g., via Swern oxidation or using a Dess-Martin periodinane, pyridinium chlorochromate, Jones reagent or Collins reagent) and/or to remove one or more hydroxyl protecting groups.

Hydroxyl protecting groups or carbonyl protecting groups (e.g., cyclic ketals, such as ethylenedioxy), if used, can be removed either prior to or after lactone ring opening. In some embodiments, one or more protecting groups can be removed prior to ring opening (i.e., prior to contacting the lactone with a nucleophile). In some embodiments, the protecting group(s) can be removed prior to the ring-closing metathesis reaction. In some embodiments, for example when silyl ethers, such as but not limited to, TBDMS groups, are used as hydroxyl protecting groups, they can be removed by reacting the compound of Formula (I), Formula (II) or the ring-opened compound with reagents, such as, but not limited to, $NH_4HF_2$, trifluoroacetic acid, tetrabutylammonium fluoride and tetrabutylammonium chloride, or any other suitable reagents known to remove the hydroxyl protecting group.

IV. Methods of Treating Disorders

Prostanoids are known to cause a wide variety of biological effects, including stimulating smooth muscle, inhibiting gastric secretions, decongesting nasal passages, decreasing blood platelet adhesion, accelerating the growth of epidermal cells, and causing various effects regarding the reproductive organs of mammals. See e.g., U.S. Pat. No. 4,049,648. In view of these effects, prostaglandins and their analogs have number of therapeutic uses, such as, but not limited to, the treatment of glaucoma and ocular hypertension, to treat ulcers (e.g., peptic ulcers), to reduce pain, to regulate inflammation and/or fever, and to induce and/or accelerate labor. Prostaglandins can also be used to treat egg binding in birds and reptiles.

In some embodiments, the presently disclosed subject matter provides compounds that can act as prostaglandin prodrugs or otherwise mimic the effects of a prostaglandin or prostaglandin analog in vivo. In some embodiments, the presently disclosed subject matter provides a compound of Formula (II), (IIa), or (IIb) which can act as a prostaglandin prodrug. The term "prostaglandin prodrug" refers to a compound that, upon administration to a recipient, is capable of providing (directly or indirectly) a biologically active prostaglandin or prostaglandin analog or an active metabolite or residue thereof. For example, in vivo, the lactone ring of the compounds of Formulas (II), (IIa) and (IIb) can hydrolyze via the action of nucleophiles (e.g., water) or enzymes (e.g., esterases) present under biological conditions to form active prostaglandins or analogs or metabolites thereof.

Use of lactone prodrugs can result in a decrease in side effects associated with administering the corresponding prostaglandins. For example, intravenous infusion of lactones can allow for higher infusion rates compared to infusion rates of the free carboxylic acid of the corresponding prostaglandin. Intramuscular administration of lactones can provide a more consistent release rate and/or a more prolonged duration of release than the corresponding free acid. In addition, the lactones can have improved chemical stability and can result in a lower incidence of undesirable gastrointestinal and bronchopulmonary side effects (e.g., nausea) than the corresponding prostaglandin.

Thus, in some embodiments, the compound of Formula (II), (IIa) or (IIb) can be formulated into a pharmaceutical composition (e.g., with a pharmaceutically acceptable carrier) and administered to a subject, such as a mammal or other vertebrate, to treat a disease or condition treatable by a prostaglandin or prostaglandin analog, such as, but not limited to, glaucoma, ocular hypertension, pulmonary hypertension, inadequate eyelash/eyebrow growth (e.g., hypotrichosis), egg binding (e.g., in reptiles and birds), ulcer (e.g., peptic ulcers), pain, fever, or inflammation. In some embodiments, administration of the compound of Formula (II), (IIa) or (IIb) can induce and/or accelerate labor or treat another gynecological/obstetrics-related condition (e.g., postpartum hemorrhage). Thus, the compounds can also be used to treat diseases or conditions in pregnant mammalian subjects wherein the induction and/or acceleration of labor would be beneficial to mother and/or child. Such diseases and conditions include, for example, eclampsia, pre-eclampsia, HELLP syndrome, gestational diabetes, placental abrubtion, fetal distress, prolonged labor, and the like. Additional diseases or conditions treatable by prostaglandins are described, for example, in U.S. Pat. No. 4,049,648.

In some embodiments, the presently disclosed subject matter provides a method of treating a disease or condition treatable by administration of a prostaglandin, the method comprising administering to a subject in need of treatment thereof a compound of Formula (II):

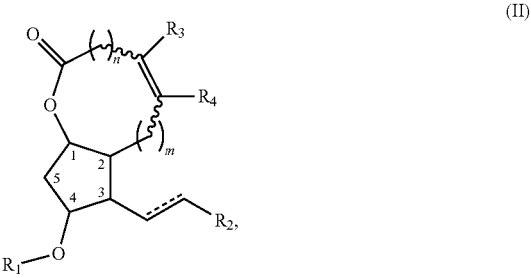

wherein:
n and m are independently integers between 0 and 10;
$R_1$ is H or a hydroxyl protecting group;
$R_2$ is selected from the group including, but not limited to, H, alkyl and aralkyl, optionally wherein the alkyl or aralkyl group further comprises one or more alkyl or aryl group substituents; and
$R_3$ and $R_4$ are independently selected from the group including, but not limited to, H, alkyl, aralkyl, and aryl, optionally wherein the alkyl, aralkyl, or aryl group further comprises one or more alkyl or aryl group substituents.

In some embodiments, the substituents at carbon 1 and carbon 2 are oriented cis to one another. In some embodiments, the substituents at carbon 3 and carbon 4 are oriented trans to one another. Thus, in some embodiments, the compound of Formula (II) is a compound of Formula (IIa) or (IIb):

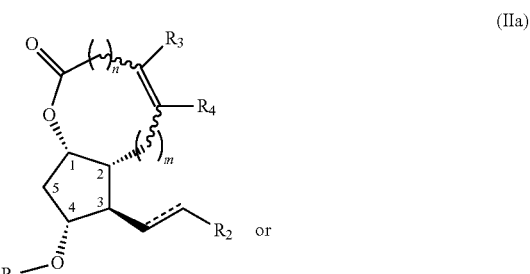

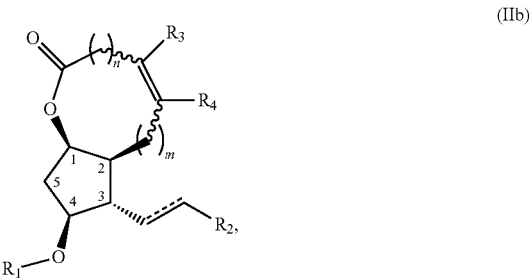

wherein:
n and m are independently integers between 0 and 10;
$R_1$ is H or a hydroxyl protecting group;
$R_2$ is selected from the group including, but not limited to, H, alkyl and aralkyl, optionally wherein the alkyl or aralkyl group further comprises one or more alkyl or aryl group substituents; and $R_3$ and $R_4$ are independently selected from the group including, but not limited to, H, alkyl, aralkyl, and aryl, optionally wherein the alkyl, aralkyl, or aryl group further comprises one or more alkyl or aryl group substituents.

In some embodiments, $R_2$ is alkyl or aralkyl, wherein the alkyl or aralkyl group further comprises a branched alkyl group and/or one or more alkyl and/or aryl group substituents selected from the group including, but not limited to, carbonyl, halo, hydroxyl, protected hydroxyl, alkyl, alkoxyl, aryloxyl, and amino (e.g., —$NH_2$, protected amino, alkylamino, dialkylamino, arylamino, acylamino or another functionalized amino group). In some embodiments, $R_2$ can be substituted by two alkyl group substituents which together form an alkylene group (e.g., an ethylenedioxy, propylenedioxy, or ethylenedithio group).

In some embodiments, $R_2$ is a group of the formula:

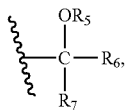

wherein $R_5$ is H or a hydroxyl protecting group; $R_6$ is H or alkyl; and $R_7$ is selected from the group including, but not limited to, alkyl (e.g., branched or straight chain alkyl), $(CH_2)_q R_8$, and $(CH_2)_q OR_8$, wherein q is an integer from 0 to 4 (i.e., 0, 1, 2, 3, or 4) and $R_8$ is alkyl optionally substituted with one or more alkyl group substituents or aryl, optionally substituted with one or more aryl group substituents (e.g., halo, alkyl, substituted alkyl (e.g., haloalkyl)).

In some embodiments, $R_1$ and $R_5$ are the both H. In some embodiments, $R_5$ is H and $R_6$ is H or methyl. In some embodiments, $R_7$ is selected from the group comprising 2-phenylethyl, benzothienyl, pentyl, (2-methyl)hexyl), —$CH_2$O-phenyl, —$CH_2$—O-phenyl-Cl, and —$CH_2$—O-phenyl-$CF_3$.

In some embodiments, $R_2$ is —$CF_2CH_2$O-phenyl or

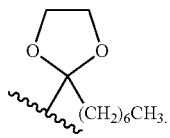

In some embodiments, one or both of $R_3$ and $R_4$ are straight chain, branched, or substituted alkyl. In some embodiments, $R_3$ and/or $R_4$ are H.

The variable n can be any integer between 0 and 10 (i.e., 0, 1, 2, 3, 4, 5, 6, 7, 8, 9, or 10). In some embodiments, n is 2 or 3. In some embodiments, n is 0.

The variable m can be any integer between 0 and 10 (i.e., 0, 1, 2, 3, 4, 5, 6, 7, 8, 9, or 10). In some embodiments, m is between 1 and 10. In some embodiments, m is 1. In some embodiments, m is 4.

The sum of variables n and m can be any integer between 0 and 20 (i.e., n+m can be 0, 1, 2, 3, 4, 5, 6, 7, 8, 9, 10, 11, 12, 13, 14, 15, 16, 17, 18, 19, or 20). In some embodiments, n+m=3 or 4 and the lactone of Formula (II) is a nine- or ten-membered ring.

The double bond of the lactone ring of the compounds of Formula (II), (IIa), or (IIb) can be cis or trans with regard to the orientation of the substituents that form the ring (i.e., the substituents that include the —$(CH_2)_n$— and —$(CH_2)_m$— groups). When the lactone ring is smaller (e.g., m+n is 4 or less), the double bond substituents that are part of the ring can be on the same side of the double bond in order to reduce ring strain. Thus, in some embodiments, wherein m+n is 4 or less, the double bond of the lactone is cis. When the lactone ring is larger, the double bond can be cis or trans with regard to the orientation of the substituents that form the ring. Thus, in some embodiments, wherein m+n is greater than 4, the double bond is trans. In some embodiments, wherein m+n is greater than 4, the double bond is cis.

In some embodiments, the presently disclosed subject matter provides a method of treating a disease or condition treatable by administration of a prostaglandin, the method comprising administering to a subject in need of treatment thereof a compound of Formula (II), wherein the compound of Formula (II) is selected from the group consisting of:

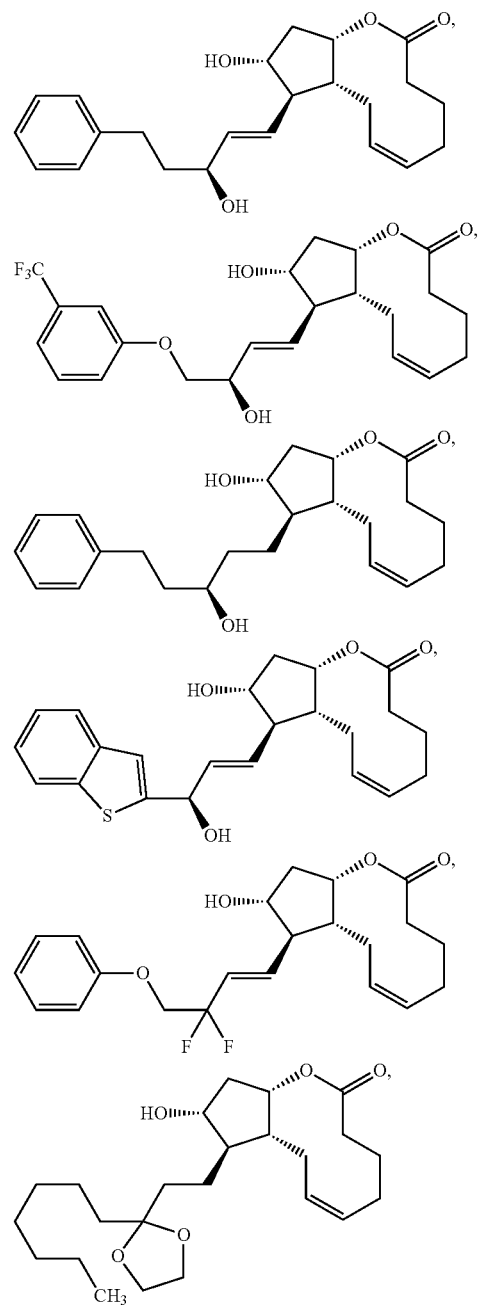

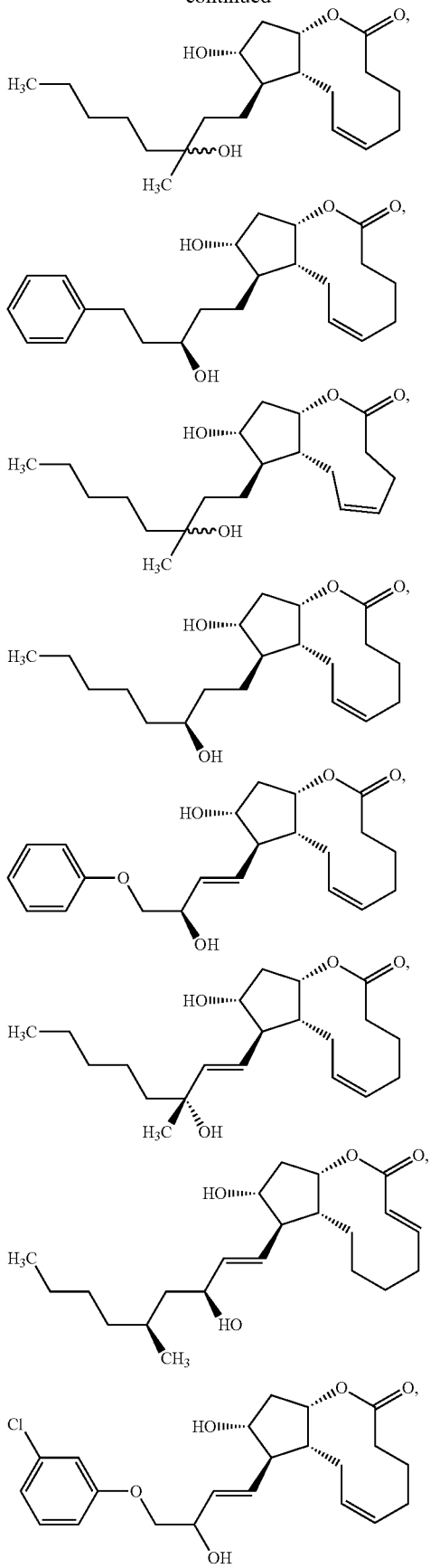
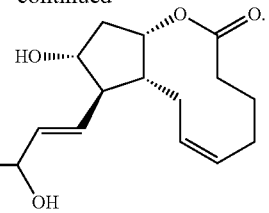

The presently described compounds can be administered as pharmaceutically acceptable salts and/or as solvates. Pharmaceutically acceptable salts are described, for example, in Berge et al., (J. Pharm. Sci., 66(1), 1-19 (1977)). The term "pharmaceutically acceptable" can refer to salts (or carriers) that are pharmaceutically acceptable in humans.

Thus, in some embodiments, the presently disclosed compound, their salt and/or solvates, can be admixed with a pharmaceutically acceptable carrier, e.g., to provide a pharmaceutical formulation or composition. Pharmaceutical formulations can be prepared for oral, intravenous, intramuscular, topical, or aerosol administration as discussed in greater detail below. Thus, in some embodiments, the formulations can be prepared in dosages forms, such as but not limited to, tablets, capsules, liquids (solutions or suspensions), suppositories, ointments, creams, or aerosols. In some embodiments, the presently disclosed subject matter provides such compounds that have been lyophilized and that can be reconstituted to form pharmaceutically acceptable formulations for administration, for example, as by intravenous or intramuscular injection.

The therapeutically effective dosage of any specific compound, the use of which is within the scope of embodiments described herein, will vary somewhat from compound to compound, and patient to patient, and will depend upon the condition of the patient and the route of delivery.

For example, for topical administration of the presently disclosed compounds in ophthalmic solutions directly to the eye, the presently disclosed compounds can be formulated at between about 0.00003 to about 3 percent by weight in aqueous solution buffered at a pH of between about 4.5 and about 8.0 or at a pH of between about 7.0 and about 7.6. The dosage range can be between about 0.1 and about 100 micrograms per eye per day. In some embodiments, the dosage range can be between about 1 and about 10 micrograms per eye per day.

For additional example, for treatment of ulcers, the presently disclosed compounds can be injected or infused intravenously, subcutaneously, or intramuscularly in an infusion dose range of about 0.1 to about 500 micrograms per kg body weight per minute, or a total daily dose by injection or infusion of about 0.1 to about 20 mg per kg body weight per day.

In accordance with the present methods, the compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the compound or salt should be in the form of a plurality of solid particles or droplets having a particle size from about 0.5 to about 5 microns, and preferably from about 1 to about 2 microns.

When the pharmaceutical composition is to be administered in a solution, water is the carrier of choice with respect to water-soluble compounds or salts. With respect to the water-soluble compounds or salts, an organic vehicle, such as glycerol, propylene glycol, polyethylene glycol, or mixtures thereof, can also be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In some embodiments, the pharmaceutical formulations of the presently disclosed subject matter can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising one or more of the presently disclosed compounds or salts thereof, in a unit dosage form in a sealed container. The compound(s) or salt(s) is provided in the form of a lyophilizate, which is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has solubility in water of less than about 20 mg/mL. In some embodiments, water-soluble compounds or salts can be desirable whereas in other embodiments water-insoluble compounds or salts likewise can be desirable.

The subject treated in the presently disclosed subject matter in its many embodiments is desirably a human subject, although it is to be understood the methods described herein are effective with respect to all vertebrate species (e.g., mammals, reptiles (such as turtles), and birds), which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos or as pets (e.g., parrots), as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Synthesis of Bimatoprost

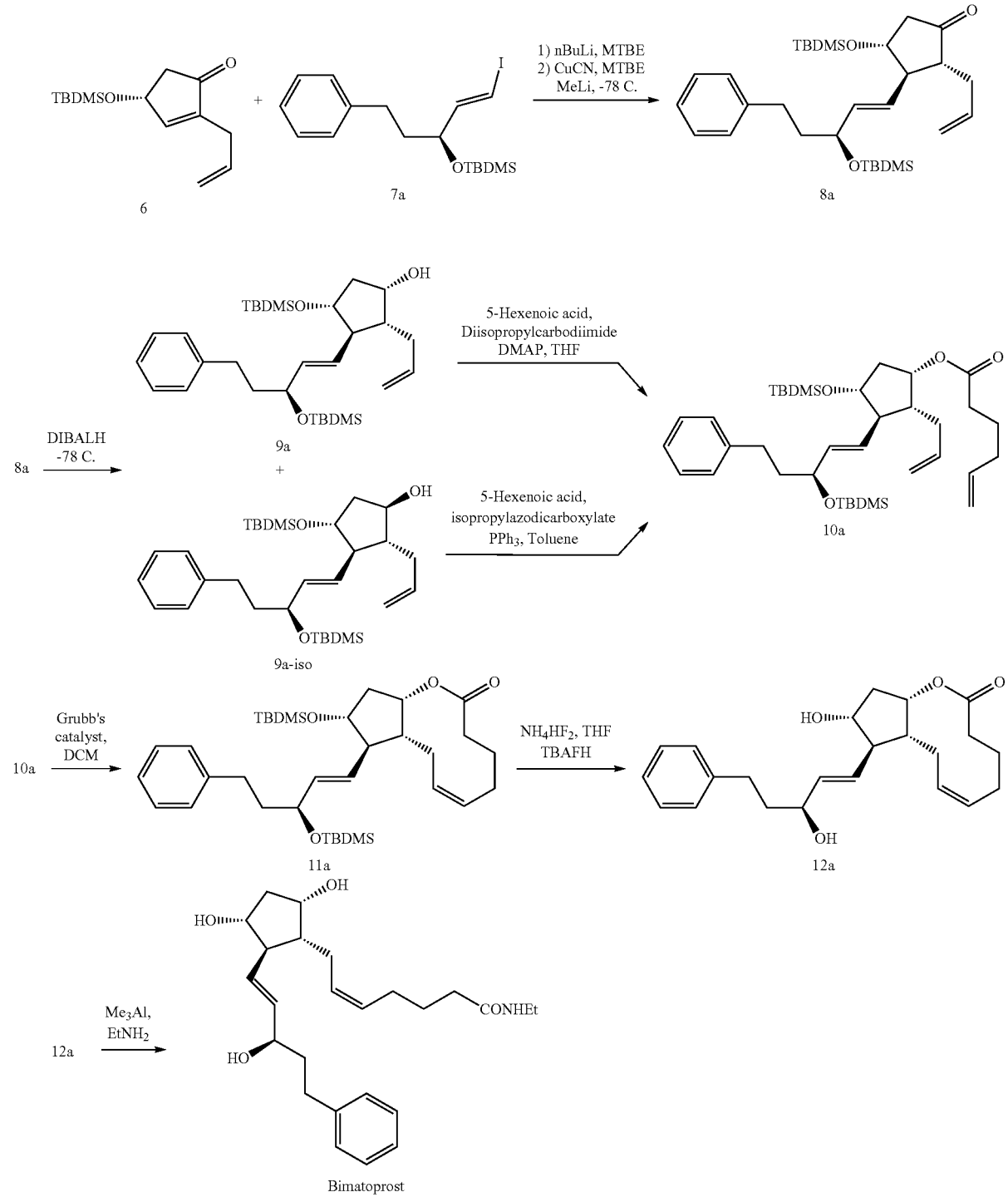

Synthesis of Bimatoprost.

An exemplary synthesis of bimatoprost, a prostaglandin analog, is shown in Scheme 3. The synthesis is scalable, highly convergent and includes a conjugate addition between two chiral synthons, cyclopentenone derivative 6 and vinyl iodide 7a to form ketone 8a. 7a and similar vinyl halides can be prepared in a manner analogous to that shown for the corresponding THP-protected vinyl iodide in U.S. Pat. No. 7,109,371 to Clissold et al., or by other methods known in the art. Ketone 8a is reduced to the corresponding isomeric alcohols 9a and 9a-iso, followed by esterification with 5-hexenoic acid to produce ester intermediate 10a. A single isomer of the alcohol can be produced, if desired, by using a stereoselective reducing agent, such as a SELECTRIDE™ (Sigma-Aldrich, St. Louis, Mo., United States of America) reducing agent. Ring-closure metathesis (RCM) of 10a produced 10-membered ring lactone 11a, which was subsequently deprotected to form lactone 12a. Ring-opening of lactone 12a with ethylamine produced Bimatoprost. The overall yield of Bimatoprost starting from 6 and 7a was good, with each step having a yield of about 60% or greater.

Individual steps in the synthesis of Bimatoprost are described further hereinbelow in Examples 5-10. An alternative step for the synthesis of ketone 8a, using an alkyne reagent, is also shown hereinbelow in Example 13. Ring-opening of 11a prior to deprotection to form a hydroxy-protected Bimatoprost and its subsequent deprotection are described in Examples 11 and 12. As shown below in Schemes 4-6 of Examples 2-4, other exemplary prostanoids were prepared via analogous routes as that shown in Scheme 3. Details regarding individual steps in these syntheses are also shown hereinbelow in Examples 5-10.

Example 2

Synthesis of Travoprost

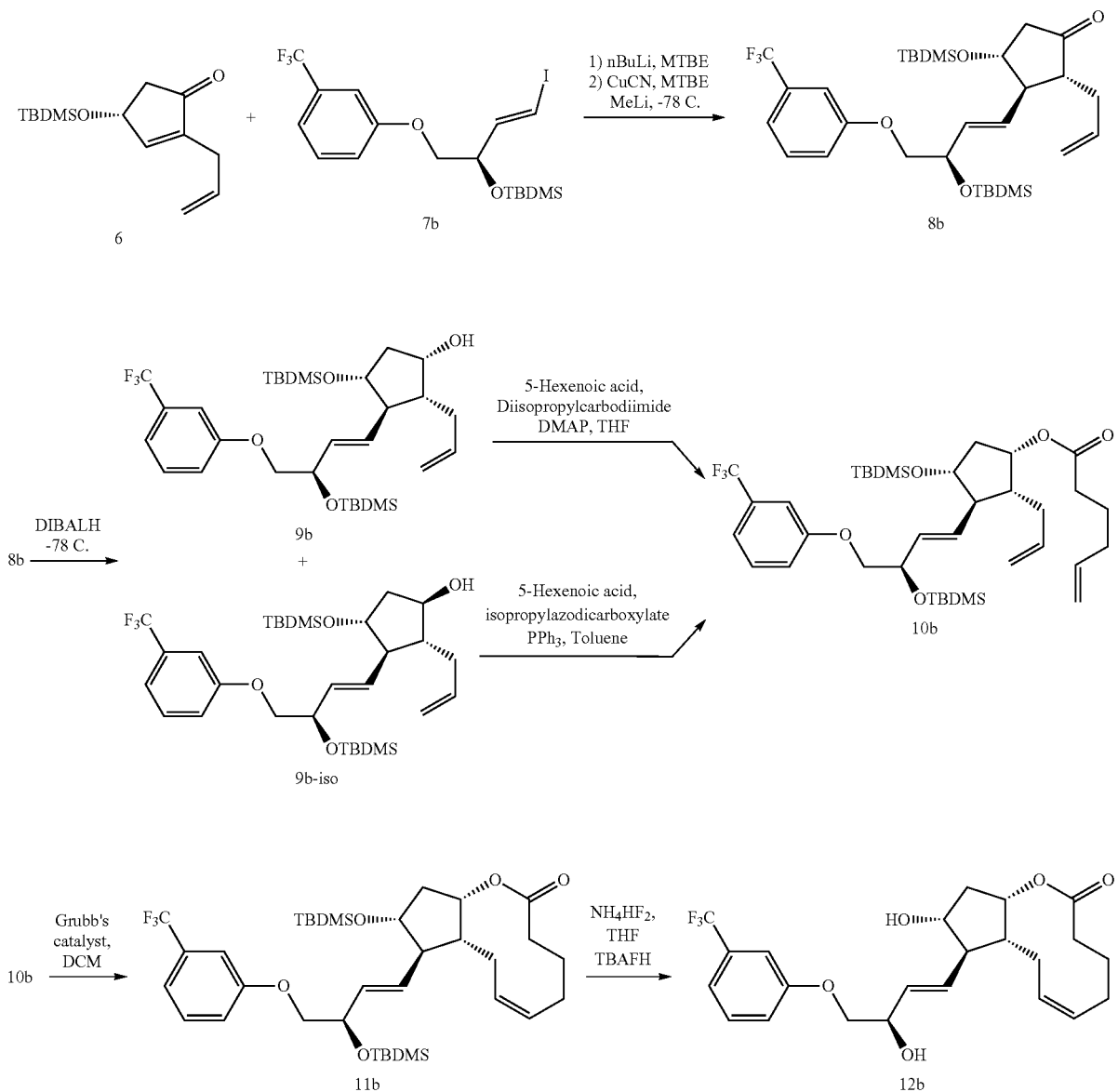

Synthesis of Travoprost.

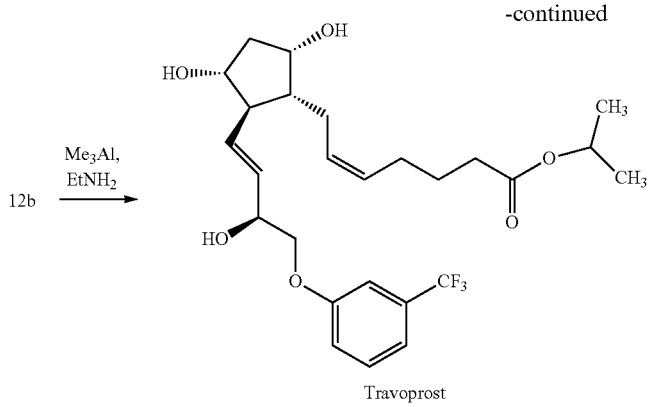
Travoprost
Example 3
Synthesis of Latanoprost
Scheme 5. Synthesis of Latanoprost.
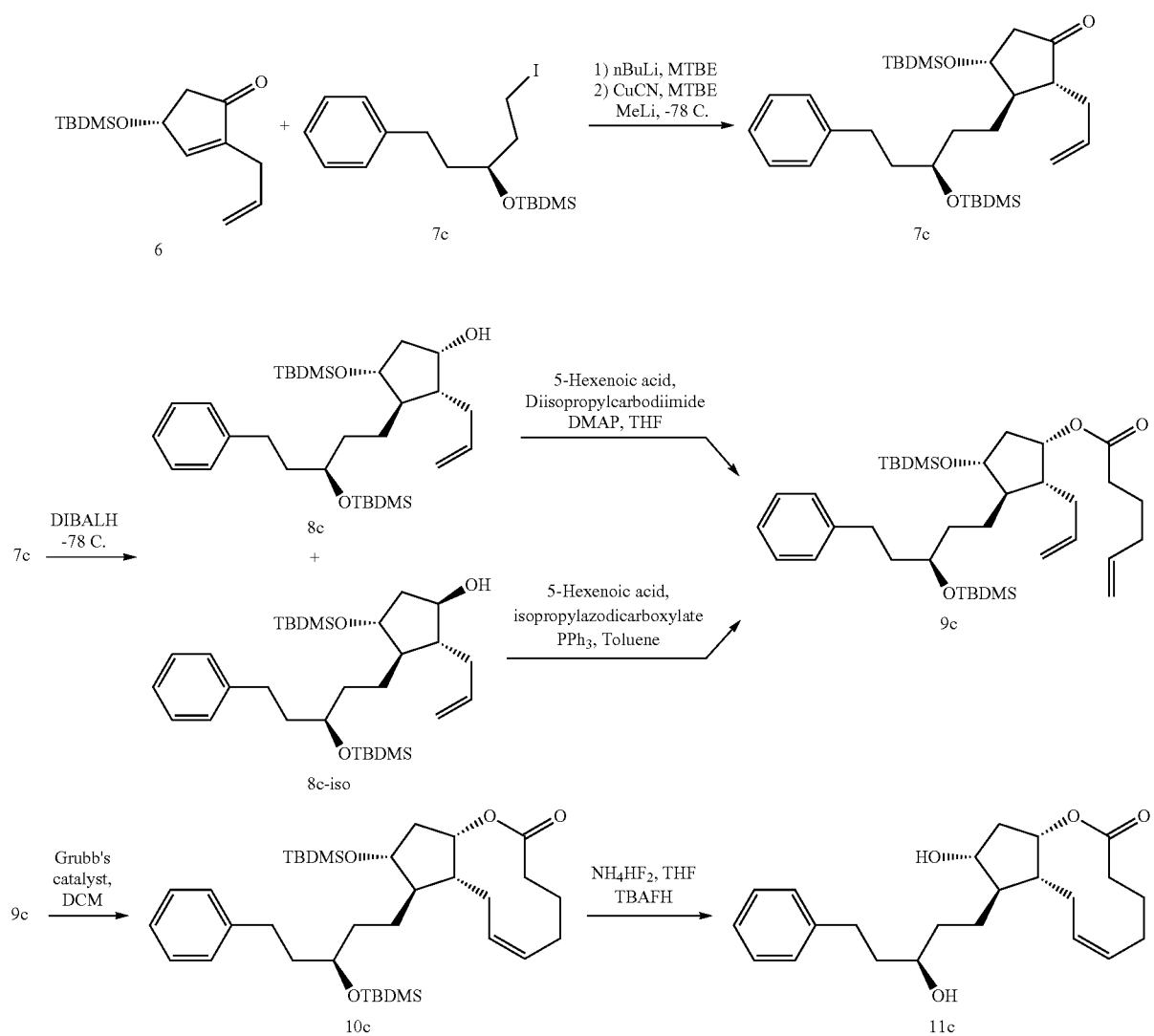

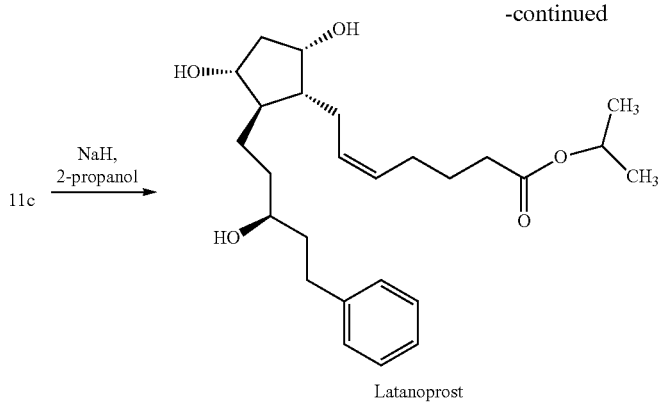
Latanoprost
Example 4
Synthesis of 13,14-Dihydro-15-(2-benzothienyl)-15-pentanor PGF$_{1\alpha}$
Scheme 6. Synthesis of 13, 14-dihydro-15-(2-benzothienyl)-15-pentanor PGF$_{1a}$.
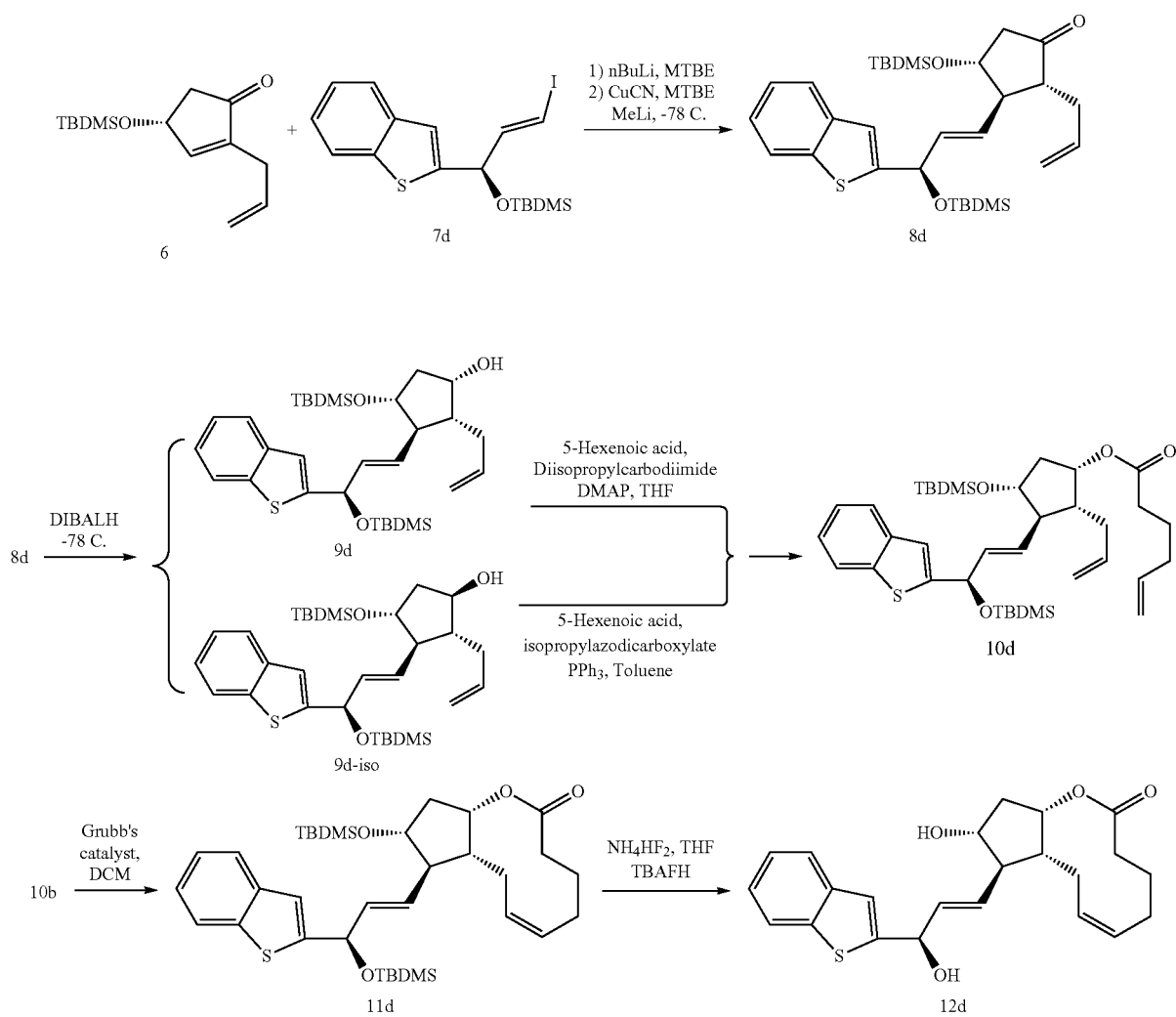

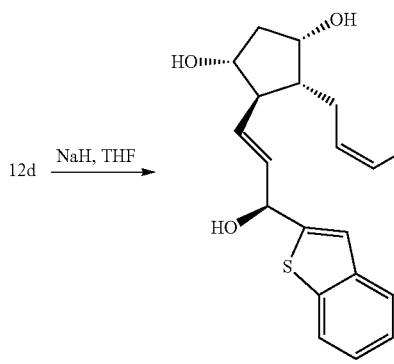
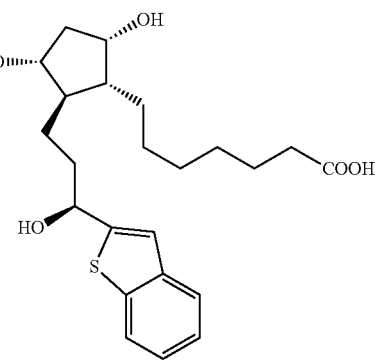

13,14-dihydro-15-(2-benzothienyl)-
15-pentanor PGF$_{1a}$

Example 5

Synthesis of Ketones 8a-8d

Synthesis of Ketone 8a:

As shown above in Scheme 3 in Example 1, a 500 mL 3-necked round-bottom flask, equipped with a magnetic bar, a temperature probe, rubber septa, and a nitrogen gas inlet was charged at room temperature with 31.7 g (78.8 mmol) of vinyl iodide 7a in 150 mL of MTBE. The reaction flask was cooled to −78° C. and while stirring 33 mL (82.7 mmol) of 2.5 M n-butyl lithium in hexanes was added. The mixture was allowed to stir at −78° C. for 2 h. A separate 3.0 L 3-necked round-bottom flask, equipped with a magnetic bar, a temperature probe, rubber septa, and a nitrogen gas inlet was charged, at room temperature, with 7.4 g (82.7 mmol) CuCN and 200 mL of MTBE. The stirring suspension was cooled to −78° C. and 51.7 mL (82.7 mmol) of methyl lithium, 1.6 M in THF, were slowly added over 10 min. The mixture was allowed to warm to −15° C. while stirring for 30 min, giving a clear cuprate solution. The cuprate solution was then cooled to −78° C. and the vinyl lithium solution, prepared earlier in the 500 mL flask, was added via cannula. The resulting solution was allowed to warm to −40° C., stirred for 30 min at −40° C. and then cooled again to −78° C., followed by a slow addition of 15.0 g (59.1 mmol) of the cyclopentenone reagent 6, dissolved in 120 mL of MTBE. The resulting mixture was stirred at −78° C. for 45 min before it was quenched by a slow addition of 100 mL of saturated ammonium chloride. Then cooling was removed, the reaction mixture warmed to room temperature, and the layers were separated. The organic layer was washed twice with a mixture of 250 mL of saturated ammonium chloride and 25 mL of concentrated ammonium hydroxide. The combined aqueous layers were washed with 200 mL MTBE. The combined organic layers were washed with 200 mL of brine, dried over sodium sulfate, filtered, concentrated and purified by column chromatography to obtain 31 g, (99.4% yield) of pure cyclopentenone derivative 8a, confirmed by $^1$H NMR.

Synthesis of Ketone 8b:

As shown in Scheme 4 in Example 2, a 250 mL 3-necked round-bottom flask equipped with a magnetic bar, a temperature probe, rubber septa, and a nitrogen gas inlet was charged at room temperature with 8.1 g (17.1 mmol) of vinyl iodide 7b in 40 mL of MTBE. The reaction flask was cooled to −78° C. and while stirring 7.2 mL (17.9 mmol) of 2.5 M n-butyl lithium in hexanes was added. The mixture was allowed to stir at −78° C. for 2.5 h. A separate 2.0 L 3-necked round-bottom flask equipped with a magnetic bar, a temperature probe, rubber septa, and a nitrogen gas inlet was charged, at room temperature, with 1.6 g (17.9 mmol) CuCN, and 60 mL of MTBE. The stirring suspension was cooled to −78° C. and 11.2 mL (17.9 mmol) of methyl lithium, 1.6 M in THF, were slowly added over 10 min. The mixture was allowed to warm to −15° C. while stirring for 30 min giving a clear solution. The cuprate solution was then cooled to −78° C. and the vinyl lithium solution, prepared earlier in the 250 mL flask, was added via cannula. The resulting solution was allowed to warm to −40° C., stirred for 30 min at −40° C. and then cooled again to −78° C., followed by slow addition of 3.5 g (13.7 mmol) of cyclopentanone 6, dissolved in 30 mL of MTBE. The resulting mixture was stirred at −78° C. for 45 min before it was quenched by slow addition of 30 mL saturated ammonium chloride. Then cooling was removed, the reaction mixture warmed to room temperature, and the layers were separated. The organic layer was washed twice with a mixture of 100 mL saturated ammonium chloride and 10 mL concentrated ammonium hydroxide. The combined aqueous layers were washed with 100 mL of MTBE. The combined organic layers were washed with 100 mL of brine, dried over sodium sulfate, filtered, concentrated, and purified by column chromatography to obtain 5.8 g (70.7% yield) of cyclopentanone derivative 8b, confirmed by $^1$H NMR.

Synthesis of 8c:

As shown in Scheme 5 in Example 3, a 1.0 L 3-necked round-bottom flask equipped with a magnetic bar, a temperature probe, rubber septa, and a nitrogen gas inlet was charged at room temperature with 32 g (79.2 mmol) of iodide 7c in 400 mL of ether. The reaction flask was cooled to −78° C. and while stirring, 97.7 mL (162 mmol) of 1.7 M t-butyl lithium in hexanes was added. The mixture was allowed to stir at −78° C. for 4 h. A separate 3.0 L 3-necked round-bottom flask, equipped with a magnetic bar, a temperature probe, rubber septa, and a nitrogen gas inlet, was charged, at room temperature, with 7.4 g (83.1 mmol) CuCN, and 500 mL of MTBE. The stirring suspension was cooled to −78° C. and the vinyl lithium solution, prepared earlier in the 500 mL flask, was added via cannula. The mixture was allowed to warm to −15° C. while stirring for 30 min giving a clear solution. The cuprate solution was then cooled to −78° C., followed by a slow addition of 15.1 g (59.4 mmol) of cyclopentanone 6, dissolved in 120 mL of MTBE. The resulting mixture was stirred at −78° C. for 45 min and warmed to −50° C. for 10 min before it was quenched by slow addition of 100 mL saturated ammonium chloride. Then cooling was removed, the reaction mixture warmed to room temperature, and the layers were separated. The organic layer was washed twice with a mixture of 250 mL saturated ammonium chloride and 25 mL of concentrated ammonium hydroxide. The combined aqueous layers were washed with 200 mL of MTBE. The combined organic layers were washed with 200 mL of brine, dried over sodium sulfate, filtered, concentrated, and purified by column chromatography to obtain 19.8 g (63.5% yield) of cyclopentanone derivative 8c, confirmed by $^1$H NMR.

Synthesis of 8d:

As shown in Scheme 6 in Example 4, a 100 mL 3-necked round-bottom flask equipped with a magnetic bar, a temperature probe, rubber septa, and a nitrogen gas inlet was charged at room temperature with 2.85 g (6.61 mmol) of vinyl iodide 7d in 20 mL of MTBE. The reaction flask was cooled to −78° C. and while stirring 2.8 mL (6.95 mmol) of 2.5 M n-butyl lithium in hexanes was added. The mixture was allowed to stir at −78° C. for 2.5 h. A separate 500 L 3-necked round-bottom flask, equipped with a magnetic bar, a temperature probe, rubber septa, and a nitrogen gas inlet, was charged, at room temperature, with 0.62 g (6.95 mmol) CuCN and 20 mL of MTBE. The stirring suspension was cooled to −78° C. and 4.4 mL (6.95 mmol) of methyl lithium, 1.6 M in THF, were slowly added over 10 min. The mixture was allowed to warm to −15° C. with stirring for 30 min, giving clear solution. The cuprate solution was then cooled to −78° C. and the vinyl lithium solution, prepared earlier in the 100 mL flask, was added via cannula. The resulting solution was allowed to warm to −40° C., stirred for 30 min at −40° C., and then cooled again to −78° C., followed by a slow addition of 1.35 g (5.29 mmol) of cyclopentanone 6, dissolved in 10 mL of MTBE. The resulting mixture was stirred at −78° C. for 45 min before it was quenched by slow addition of 10 mL saturated ammonium chloride. Then cooling was removed, the reaction mixture warmed to room temperature, and the layers were separated. The organic layer was washed twice with a mixture of 20 mL saturated ammonium chloride and 2 mL concentrated ammonium hydroxide. The combined aqueous layers were washed with 30 mL of MTBE. The combined organic layers were washed with 30 mL of brine, dried over sodium sulfate, filtered, concentrated, and purified by column chromatography to obtain 2.0 g (55.5% yield) of cyclopentanone derivative 8d, confirmed by $^1$H NMR.

Example 6

Synthesis of Alcohols 9a-9d and their Isomers

Synthesis of Alcohols 9a and 9a-Iso:

As shown in Scheme 3 in Example 1, a 2.0 L 3-necked round-bottom flask equipped with a magnetic bar, a temperature probe, rubber septa, and a nitrogen gas inlet was charged at room temperature with 31 g (58.6 mmol) of compound 8a in 300 mL of toluene. The reaction flask was cooled to −78° C. and while stirring 59 mL (88 mmol) of 1.5 M DiBALH in toluene was added. The mixture was stirred for 3 h at which time thin layer chromatograph (TLC) analysis indicated complete reaction. The reaction mixture was quenched with 25 mL of methanol followed by 80 mL of 2NH$_2$SO$_4$ keeping the temperature below −50° C. The mixture was slowly warmed to room temperature and the layers were separated and organic layer washed with 80 mL of 2NH$_2$SO$_4$. The combined aqueous layers were back extracted with 200 mL of MTBE. The combined organic layers were washed with 200 mL of NaHCO$_3$, 200 mL of brine, dried over sodium sulfate, filtered, concentrated, and purified by column chromatography to obtain 15.8 g (50.8% yield) of secondary alcohol 9a, confirmed by $^1$H NMR. Isomer 9a-iso (10.7 g, 34.4% yield) was also isolated.

Alternate Synthesis of Alcohol 9a:

A 2.0 L 3-necked round-bottom flask, equipped with a magnetic stirring bar, a temperature probe, nitrogen inlet, and rubber septa, was charged, under nitrogen, with 88 mL (88 mmol) of L-SELECTRIDE™ (Sigma-Aldrich, Biotechnology LP, St. Louis, Mo., United States of America), 1M in THF, and cooled to −78° C. To this flask was slowly added a solution of 23.2 g (43.9 mmol) of compound 8a in 300 mL of THF over 2 h. The mixture continued to stir at −78° C. for another 4 h at which time TLC analysis (hexanes/ethyl acetate, 10:1) indicated complete reaction. After quenching with 300 mL of ammonium chloride, the mixture was allowed to warm to room temperature. The layers were separated and the organic layer was washed twice with a mixture of 200 mL saturated ammonium chloride and 20 mL ammonium hydroxide. The combined aqueous layers were back extracted with 200 mL MTBE. The combined organic layers were washed with 200 mL brine, dried over sodium sulfate, filtered, concentrated and purified by column chromatography to obtain 21.9 g (93.3% yield) of pure secondary alcohol 9a, confirmed by $^1$H NMR.

Synthesis of Alcohols 9b and 9b-Iso:

As shown in Scheme 4 in Example 2, a 250 mL 3-necked round-bottom flask equipped with a magnetic bar, a temperature probe, rubber septa, and a nitrogen gas inlet was charged at room temperature with 5.8 g (9.7 mmol) of compound 8b in 60 mL of toluene. The reaction flask was cooled to −78° C. and, while stirring, 10 mL (14.5 mmol) of 1.5 M DiBALH in toluene was added. The mixture was stirred for 3 h at which time TLC analysis indicated complete reaction. The reaction mixture was quenched with 5 mL of methanol followed by 20 mL of 2NH$_2$SO$_4$ keeping the temperature below −50° C. The mixture was slowly warmed to room temperature and the layers were separated and the organic layer washed with 20 mL of 2NH$_2$SO$_4$. The combined aqueous layers were back extracted with 50 mL of MTBE. The combined organic layers were washed with 80 mL of NaHCO$_3$, 80 mL of brine, dried over sodium sulfate, filtered, concentrated, and purified by column chromatography to obtain 3.0 g (51.7% yield) of secondary alcohol 9b, confirmed by $^1$H NMR. Isomer 9b-iso (2.3 g, 39.6% yield) was also isolated.

Synthesis of 9c and 9c-Iso:

As shown in Scheme 5 in Example 3, a 1.0 L 3-necked round-bottom flask equipped with a magnetic bar, a temperature probe, rubber septa, and a nitrogen gas inlet was charged at room temperature with 19.8 g (37.3 mmol) of compound 8c in 200 mL of toluene. The reaction flask was cooled to −78° C. and while stirring 38 mL (56 mmol) of 1.5 M DiBALH in toluene was added. The mixture was stirred for 3 h at which time TLC analysis indicated complete reaction. The reaction mixture was quenched with 15 mL of methanol followed by 50 mL of 2NH$_2$SO$_4$ keeping the temperature below −50° C. The mixture was slowly warmed to room temperature and the layers were separated and the organic layer washed with 50 mL of 2NH$_2$SO$_4$. The combined aqueous layers were back extracted with 150 mL of MTBE. The combined organic layers were washed with 100 mL of NaHCO$_3$, 100 mL of brine, dried over sodium sulfate, filtered, concentrated, and purified by column chromatography to obtain 12.3 g (62.1% yield) of secondary alcohol 9c, confirmed by $^1$H NMR. Isomer 9c-iso (5.0 g, 25.3% yield) was also isolated.

Synthesis of 9d and 9d-Iso:

As shown in Scheme 6 in Example 4, a 100 mL 3-necked round-bottom flask equipped with a magnetic bar, a temperature probe, rubber septa, and a nitrogen gas inlet was charged at room temperature with 1.85 g (3.32 mmol) of compound 8d in 20 mL of toluene. The reaction flask was cooled to −78° C. and while stirring 3.4 mL (5.0 mmol) of 1.5 M DiBALH in toluene was added. The mixture was stirred for 3 h at which time TLC analysis indicated complete reaction. The reaction mixture was quenched with 1 mL of methanol followed by 10 mL of $2NH_2SO_4$ keeping the temperature below −50° C. The mixture was slowly warmed to room temperature and the layers were separated and the organic layer washed with 20 mL of $2NH_2SO_4$. The combined aqueous layers were back extracted with 50 mL of MTBE. The combined organic layers were washed with 50 mL of $NaHCO_3$, 50 mL of brine, dried over sodium sulfate, filtered, concentrated, and purified by column chromatography to obtain 0.85 g (46.1% yield) of secondary alcohol 9d, confirmed by $^1H$ NMR. Isomeric alcohol 9d-iso (0.8 g, 43.2% yield) was also isolated.

Example 7

Synthesis of Esters 10a-10d

Synthesis of Ester 10a:

As shown in Scheme 3 in Example 1, a 500 mL 3-necked round-bottom flask, equipped with a magnetic stirring bar, a temperature probe, rubber septa, and a nitrogen inlet, was charged, at room temperature, under nitrogen, with 15.8 g (29.8 mmol) of alcohol 9a in 100 mL of THF, 0.2 g (6.0 mmol) of N,N-dimethyl-4-aminopyridine (DMAP), 3.9 mL (32.8 mmol) of 5-hexenoic acid, and 5.5 mL (35.8 mmol) N,N-diisopropylcarbodiimide. The stirred mixture was heated at 40° C. for 24 h. TLC analysis (hexanes/ethyl acetate, 10:1) indicated complete reaction. The reaction mixture was then diluted with 100 mL of MTBE and 100 mL of water. The layers were separated and the aqueous layer was back-extracted with 130 mL of MTBE. The combined organic layers were washed with 150 mL of $NaHCO_3$, 150 mL of brine, dried over sodium sulfate, filtered, concentrated, and chromatographically purified to afford 16.3 g (87.0% yield) of ester 10a, confirmed by $^1H$ NMR.

Synthesis of Ester 10b:

As shown in Scheme 4 in Example 2, a 250 mL 3-necked round-bottom flask equipped with a magnetic bar, a temperature probe, rubber septa, and a nitrogen gas inlet was charged at room temperature with 3.0 g (5.0 mmol) of alcohol, 9b in 20 mL of THF, 0.122 g (1.0 mmol) of DMAP, 0.65 mL (5.5 mmol) of 5-hexenoic acid, and 0.95 mL (6.0 mmol) of N,N'-diisopropylcarbodiimide. The stirred mixture was heated at 40° C. for 24 h. TLC analysis indicated complete reaction. The reaction mixture was then diluted with 20 mL of MTBE and 20 mL of water. The layers were separated and the aqueous layer was back extracted with 25 mL of MTBE. The combined organic layers were washed with 25 mL of $NaHCO_3$, 25 mL of brine, dried over sodium sulfate, filtered, concentrated, and purified by column chromatography to obtain 2.6 g (75.0% yield) of ester 10b, confirmed by $^1H$ NMR.

Synthesis of Ester 10c:

As shown in Scheme 5 in Example 3, a 500 mL 3-necked round-bottom flask equipped with a magnetic bar, a temperature probe, rubber septa, and a nitrogen gas inlet was charged at room temperature with 12.3 g (23.1 mmol) of alcohol 9c in 100 mL of THF, 0.56 g (6 mmol) of DMAP, 3.6 mL (25.4 mmol) of 5-hexenoic acid, and 4.3 mL (27.7 mmol) of N,N'-diisopropylcarbodiimide. The stirred mixture was heated at 40° C. for 24 h. TLC analysis indicated complete reaction. The reaction mixture was then diluted with 100 mL of MTBE and 100 mL of water. The layers were separated and the aqueous layer was back extracted with 130 mL of MTBE. The combined organic layers were washed with 150 mL of $NaHCO_3$, 150 mL of brine, dried over sodium sulfate, filtered, concentrated, and purified by column chromatography to obtain 12.3 g (84.2% yield) of ester 10c, confirmed by $^1H$ NMR.

Synthesis of Ester 10d:

As shown in Scheme 6 in Example 4, a 100 mL 3-necked round-bottom flask equipped with a magnetic bar, a temperature probe, rubber septa, and a nitrogen gas inlet was charged at room temperature with 0.85 g (1.5 mmol) of alcohol 9d in 20 mL of THF, 0.04 g (0.3 mmol) of N,N-dimethyl-4-aminopyridine, 0.20 mL (1.65 mmol) of 5-hexenoic acid, and 0.3 mL (1.8 mmol) of N,N'-diisopropylcarbodiimide. The stirred mixture was heated at 40° C. for 24 h. TLC analysis indicated complete reaction. The reaction mixture was then diluted with 10 mL of MTBE and 10 mL of water. The layers were separated and the aqueous layer was back extracted with 15 mL of MTBE. The combined organic layers were washed with 15 mL of $NaHCO_3$, 15 mL of brine, dried over sodium sulfate, filtered, concentrated, and purified by column chromatography to obtain 0.85 g (85.0% yield) of ester 10d, confirmed by $^1H$ NMR.

Example 8

Synthesis of Lactones 11a-11d

Synthesis of Lactone 11a:

As shown in Scheme 3 in Example 1, a 5.0 L 3-necked round-bottom flask, equipped with a magnetic stirring bar, a temperature probe, rubber septa, and a nitrogen inlet, was charged at room temperature and under nitrogen, with 20 g (31.9 mmol) of ester 10a and 1.5 L of dichloromethane (DCM). The solution was purged with nitrogen for 30 min followed by the addition of 1 g of Grubb's catalyst. The stirred reaction mixture was heated at 40° C. for 18 h. TLC analysis (hexanes/ethyl acetate, 10:1) indicated complete reaction. The reaction mixture was quenched with 40 mL of ethylamine and stirred for 1 h. The reaction mixture was then diluted with 1.0 L MTBE and 1.5 L of $NaHCO_3$. The layers were separated and the aqueous layer was back extracted with 500 mL of MTBE. The combined organic layers were washed with 1.5 L of $NaHCO_3$, 1.0 L of brine, dried over sodium sulfate, filtered, concentrated, and purified by column chromatography to afford 16.2 g (85.0% yield) of lactone 11a, confirmed by $^1H$ NMR.

Synthesis of Lactone 11b:

As shown in Scheme 4 in Example 2, a 2.0 L 3-necked round-bottom flask equipped with a magnetic bar, a temperature probe, rubber septa, and a nitrogen gas inlet was charged at room temperature with 4.2 g (6.1 mmol) of ester 10b in 315 mL of DCM. The solution was purged with nitrogen for 30 min followed by the addition of 0.5 g of Grubb's catalyst. The stirred reaction mixture was heated at 40° C. for 18 h. TLC analysis indicated complete reaction. The reaction mixture was quenched with 8 mL of ethylamine and stirred for 1 h. The reaction mixture was then diluted with 250 mL of MTBE and 250 mL of $NaHCO_3$. The layers were separated and the aqueous layer was back extracted with 100 mL of MTBE. The combined organic layers were washed with 250 mL of $NaHCO_3$, 250 mL of brine, dried over sodium sulfate, filtered, concentrated, and purified by column chromatography to obtain 3.3 g (83.0% yield) of lactone 11b, confirmed by $^1H$ NMR.

Synthesis of Lactone 11c:

As shown in Scheme 5 in Example 3, a 3.0 L 3-necked round-bottom flask equipped with a magnetic bar, a temperature probe, rubber septa, and a nitrogen gas inlet was charged at room temperature with 12.2 g (19.4 mmol) of ester 10c in 1.0 L of DCM. The solution was purged with nitrogen for 30 min followed by the addition of 1 g of Grubb's catalyst. The stirred reaction mixture was heated at 40° C. for 18 h. TLC analysis indicated complete reaction. The reaction mixture was quenched with 25 mL of ethylamine and was stirred for 1 h. The reaction mixture was then diluted with 500 mL of MTBE and 600 mL of $NaHCO_3$. The layers were separated and the aqueous layer was back extracted with 200 mL of MTBE. The combined organic layers were washed with 800 mL of $NaHCO_3$, 800 mL of brine, dried over sodium sulfate, filtered, concentrated, and purified by column chromatography to obtain 9.9 g (85.0% yield) of lactone 11c, confirmed by $^1H$ NMR.

Synthesis of Lactone 11d:

As shown in Scheme 6 in Example 4, a 1.0 L 3-necked round-bottom flask equipped with a magnetic bar, a temperature probe, rubber septa, and a nitrogen gas inlet was charged at room temperature with 2.7 g (4.4 mmol) of ester derivative 10d in 210 mL of DCM. The solution was purged with nitrogen for 30 min followed by the addition of 0.27 g of Grubb's catalyst. The stirred reaction mixture was heated at 40° C. for 18 h. TLC analysis indicated complete reaction. The reaction mixture was quenched with 5 mL of ethylamine and was stirred for 1 h. The reaction mixture was then diluted with 100 mL of MTBE and 200 mL of $NaHCO_3$. The layers were separated and the aqueous layer was back extracted with 100 mL of MTBE. The combined organic layers were washed with 200 mL of $NaHCO_3$, 200 mL of brine, dried over sodium sulfate, filtered, concentrate and purified by column chromatography to obtain 0.9 g (35.0% yield) of lactone derivative 11d, confirmed by $^1H$ NMR.

Example 9

Synthesis of Deprotected Lactones 12a-12c

Synthesis of Deprotected Lactone 12a:

As shown in Scheme 3 in Example 1, a 500 mL 3-necked round-bottom flask equipped with a magnetic bar, a temperature probe, rubber septa, and a nitrogen gas inlet was charged at room temperature with 16.2 g (27.0 mmol) of lactone 11a in 200 mL of THF, 5.5 g (95.7 mmol) of ammonium hydrogen difluoride and 25 g (95.7 mmol) of tetrabutylammonium fluoride. The reaction mixture was heated at 40° C. for 24 h and TLC analysis indicated complete reaction. The mixture was diluted with 100 mL of MTBE and 200 mL of $NaHCO_3$. The layers were separated and the aqueous layer was back extracted with 100 mL of MTBE. The combined organic layers were washed with 200 mL of $NaHCO_3$, 200 mL of brine, dried over sodium sulfate, filtered, concentrated, and purified by column chromatography to obtain 6.1 g (61.0% yield) of deprotected lactone 12a, confirmed by $^1H$ NMR.

Synthesis of Deprotected Lactone 12b:

As shown in Scheme 4 in Example 2, a 250 mL 3-necked round-bottom flask equipped with a magnetic bar, a temperature probe, rubber septa, and a nitrogen gas inlet was charged at room temperature with 4.0 g (6.0 mmol) of lactone 11b in 50 mL of THF, 1.0 g (18.0 mmol) of ammonium hydrogen difluoride and 4.7 g (18.0 mmol) of tetrabutylammonium fluoride. The reaction mixture was heated at 40° C. for 24 h and TLC analysis indicated complete reaction. The mixture was diluted with 25 mL of MTBE and 50 mL of $NaHCO_3$. The layers were separated and the aqueous layer was back extracted with 25 mL of MTBE. The combined organic layers were washed with 30 mL of $NaHCO_3$, 30 mL of brine, dried over sodium sulfate, filtered, concentrated, and purified by column chromatography to obtain 1 g (38.5% yield) of deprotected lactone 12b, confirmed by $^1H$ NMR.

Synthesis of Deprotected Lactone 12c:

As shown in Scheme 5 in Example 3, a 500 mL 3-necked round-bottom flask equipped with a magnetic bar, a temperature probe, rubber septa, and a nitrogen gas inlet was charged at room temperature with 11.7 g (19.5 mmol) of lactone 11c in 120 mL of THF, 3.3 g (58.5 mmol) of ammonium hydrogen difluoride and 15.3 g (58.5 mmol) of tetrabutylammonium fluoride. The reaction mixture was heated at 40° C. for 24 h and TLC analysis indicated complete reaction. The mixture was diluted with 50 mL of MTBE and 80 mL of $NaHCO_3$. The layers were separated and the aqueous layer was back extracted with 50 mL of MTBE. The combined organic layers were washed with 80 mL of $NaHCO_3$, 80 mL of brine, dried over sodium sulfate, filtered, concentrated, and purified by column chromatography to obtain 5.3 g (72.6% yield) of deprotected lactone 12c, confirmed by $^1H$ NMR.

Synthesis of Deprotected Lactone 12d:

As shown in Scheme 6 in Example 4, a 50 mL 3-necked round-bottom flask equipped with a magnetic bar, a temperature probe, rubber septa, and a nitrogen gas inlet was charged at room temperature with 0.627 g (1.0 mmol) of lactone 11d in 25 mL of THF, 0.33 g (5.85 mmol) of ammonium hydrogen difluoride and 1.53 g (5.85 mmol) of tetrabutylammonium fluoride. The reaction mixture was heated at 40° C. for 24 h and TLC analysis indicated complete reaction. The mixture was diluted with 25 mL of MTBE and 50 mL of $NaHCO_3$. The layers were separated and the aqueous layer was back extracted with 25 mL of MTBE. The combined organic layers were washed with 40 mL of $NaHCO_3$, 40 mL of brine, dried over sodium sulfate, filtered, concentrated, and purified by column chromatography to obtain 0.32 g (77.5% yield) of deprotected lactone 12d, confirmed by $^1H$ NMR.

Example 10

Ring Opening of Deprotected Lactones

Synthesis of Bimatoprost from 12a:

As shown in Scheme 3 in Example 1, a 250 mL 3-necked round-bottom flask equipped with a magnetic bar, a temperature probe, rubber septa, and a nitrogen gas inlet was charged at room temperature with 4.1 g (11.1 mmol) of deprotected lactone 12a in 20 mL of THF, 22.2 mL (44.3 mmol) of 2 M trimethylaluminum in THF, and 67 mL (133 mmol) of 2 Methylamine in THF. The reaction mixture was heated at 40° C. for 18 h and TLC analysis indicated complete reaction. The mixture was diluted with 50 mL of water and the pH was adjusted to 6 with 1N HCl. The layers were separated and the aqueous layer was back extracted with 20 mL of ethyl acetate for two times. The combined organic layers were washed with 40 mL of brine, dried over sodium sulfate, filtered, and concentrated.

The crude product was triturated with 20 mL of MTBE at 35° C. for 3 h, cooled to room temperature, and filtered to obtain 3.1 g (67.3% yield) of Bimatoprost, confirmed by $^1H$ NMR.

Synthesis of Travoprost from 12b:

As shown in Scheme 4 in Example 2, a 100 mL 3-necked round-bottom flask equipped with a magnetic bar, a temperature probe, rubber septa, and a nitrogen gas inlet was charged at room temperature with 1.0 g (2.27 mmol) of deprotected lactone 12b in 30 mL of 2-propanol and 0.18 g (4.5 mmol) of sodium hydride, 60%, in mineral oil. The reaction mixture was heated at 35° C. for 18 h and TLC analysis indicated complete reaction. The mixture was diluted with 20 mL of water and the pH was adjusted to 6 with 1N HCl. The layers were separated and the aqueous layer was back extracted with 20 mL of 2-propanol four times. The combined organic layers were washed with 40 mL of brine, dried over sodium sulfate, filtered, and concentrated.

The concentrated material was dissolved in 20 mL of THF, 1.7 mL (11.4 mmol) of DBU and 1.2 mL (11.4 mmol) of iodopropane. The reaction mixture was stirred at room temperature for 18 h and TLC analysis indicated complete reaction. The mixture was diluted with 30 mL of isopropyl acetate and 30 mL of water. The layers were separated and the aqueous layer was back extracted with 20 mL of isopropyl acetate two times. The combined organic layers were washed with 20 mL of brine, dried over sodium sulfate, filtered, and concentrated.

The material was purified by using reverse phase biotage, 1:1 acetonitrile (ACN): H$_2$O to obtain 0.52 g (46% yield) of Travoprost, confirmed by $^1$H NMR.

Synthesis of Latanoprost from 12c:

As shown in Scheme 5 in Example 3, a 250 mL 3-necked round-bottom flask equipped with a magnetic bar, a temperature probe, rubber septa, and a nitrogen gas inlet was charged at room temperature with 7.3 g (19.6 mmol) of deprotected lactone 12c in 70 mL of 2-propanol and 1.6 g (39.2 mmol) of sodium hydride, 60%, in mineral oil. The reaction mixture was heated at 35° C. for 18 h and TLC analysis indicated complete reaction. The mixture was diluted with 60 mL of water and the pH was adjusted to 6 with 1N HCl. The layers were separated and the aqueous layer was back extracted with 40 mL of 2-propanol four times. The combined organic layers were washed with 50 mL of brine, dried over sodium sulfate, filtered, and concentrated.

The material was dissolved in 60 mL of THF, 5.0 mL (33.3 mmol) of DBU and 3.3 mL (33.3 mmol) of iodopropane. The reaction mixture was stirred at room temperature for 18 h and TLC analysis indicated complete reaction. The mixture was diluted with 60 mL of ethyl acetate and 60 mL of water. The layers were separated and the aqueous layer was back extracted with 40 mL of ethyl acetate for two times. The combined organic layers were washed with 50 mL of brine, dried over sodium sulfate, filtered, and concentrated.

The material was purified by using reverse phase biotage, 70:30 ACN:H$_2$O to obtain 4.1 g (49% yield) of Latanoprost, confirmed by $^1$H NMR.

Example 11

Synthesis of Protected Bimatoprost

Scheme 7. Synthesis of Protected Bimatoprost.

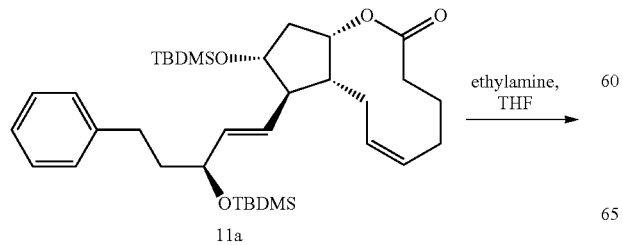

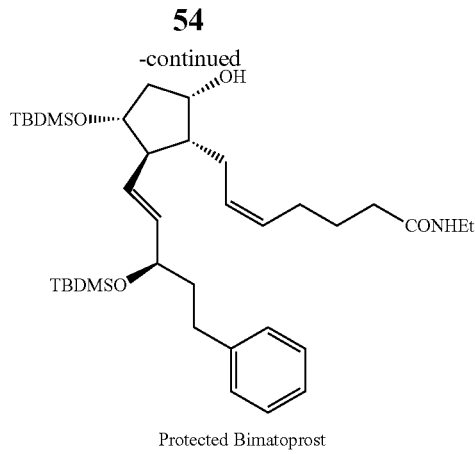

Protected Bimatoprost

As shown in Scheme 7 above, a 250 mL 3-necked round-bottom flask, equipped with a magnetic stirring bar, a temperature probe, rubber septa, and nitrogen inlet, was charged at room temperature, under nitrogen, with 3.0 g (5.01 mmol) of compound 11a in 30 mL of THF, and 15 mL ethylamine, 2.0 M in THF. The mixture heated at 40° C. for 24 h and then reflux for another 3 h. TLC analysis (hexanes/ethyl acetate, 10:1) indicated complete reaction. The mixture was cooled to room temperature and diluted with 30 mL of MTBE and 25 mL of water. The layers were separated and the aqueous layer was washed with 15 mL of MTBE. The combined organic extracts were washed with 25 mL of brine, dried over sodium sulfate, filtered, concentrated, and chromatographically purified to afford 2.90 g (90.0% yield) of bis-silylated bimatoprost, confirmed by $^1$H NMR.

Example 12

Deprotection of Protected Bimatoprost

Scheme 8. Deprotection of Protected Bimatoprost.

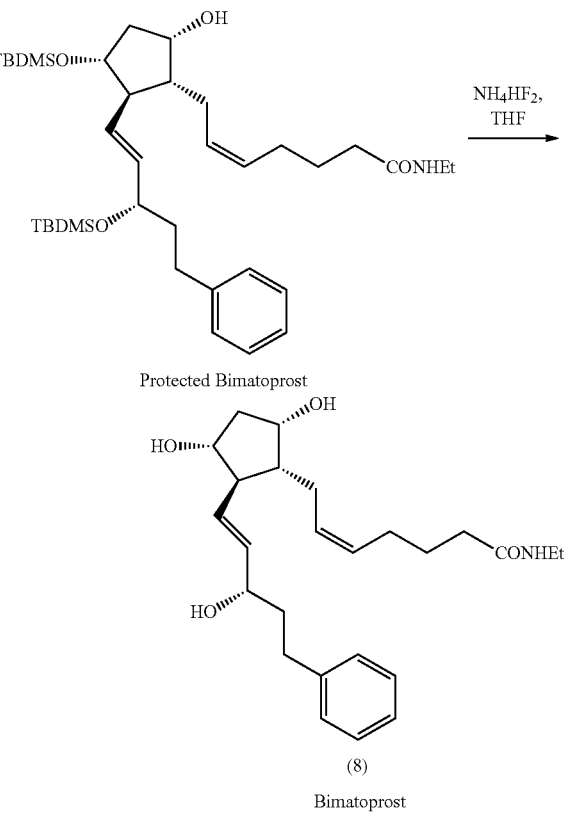

Bimatoprost

As shown in Scheme 8 above, a 250 mL 3-necked round-bottom flask, equipped with a magnetic stirring bar, a temperature probe, rubber septa, and nitrogen inlet, was charged at room temperature, under nitrogen, with 3.0 g (3.11 mmol) of protected bimatoprost from Example 12, 30 mL of THF, and 0.9 g (90.8 mmol) of ammonium hydrogen difluoride. The reaction mixture was heated at 40° C. for 24 h and TLC analysis (hexanes/ethyl acetate, 1:1) indicated complete reaction. The mixture was then diluted with 30 mL of MTBE and 25 mL of water followed by layer separation. The aqueous layer was back extracted with 15 mL of MTBE. The combined organic extracts were washed with 25 mL of brine, dried over sodium sulfate, filtered, concentrated, and chromatographically purified to afford 1.02 g (80.0% yield) of bimatoprost confirmed by $^1$H NMR.

Example 13

Synthesis of Ketone 8a Using Alkyne Reagent 7a'

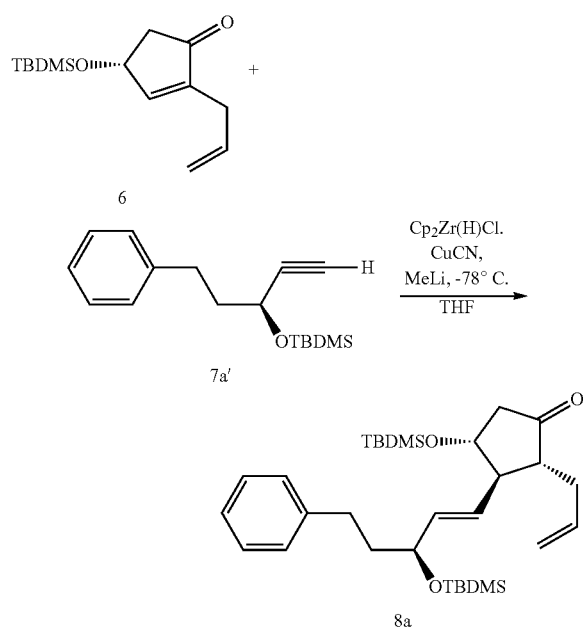

As shown in Scheme 9, a 100 mL 3-necked round-bottom flask, equipped with a magnetic bar, a temperature probe, rubber septa, and a nitrogen gas inlet was charged at room temperature with 500 mg (1.82 mmol) of compound 7a', 600 mg (2.36 mmol) of bis(cyclopentadienyl)zirconium(IV) chloride hydride (Cp$_2$Zr(H)Cl), and 3 ml of THF. The suspension was stirred at room temperature for 3 h in dark. Then it was cooled to −78° C. and, while stirring, 180 mg CuCN (2.0 mmol) was added followed by a further slow addition of 3.3 mL of 1.6 M (5.3 mmol) of methyl lithium in ether while the temperature was maintained below −70° C. The mixture was allowed to warm up to −20° C. for 1 hr before it was cooled down to −78° C. followed by the addition of 462 mg (1.82 mmol) of compound 6. The mixture was stirred at −78° C. for 30 min, quenched with 10 mL of saturated ammonium chloride, diluted with 15 mL of MTBE, and allowed to warm to room temperature. The layers were separated and the aqueous layer was back-extracted with 15 mL of MTBE. The combined organic layers were washed twice with 10 mL of brine, dried over sodium sulfate, filtered, concentrated and chromatographically purified to afford 547 mg (68% yield) of pure ketone 8a, confirmed by $^1$H NMR.

Example 14

Synthesis of 9-Membered Ring Lactones 11e and 12e

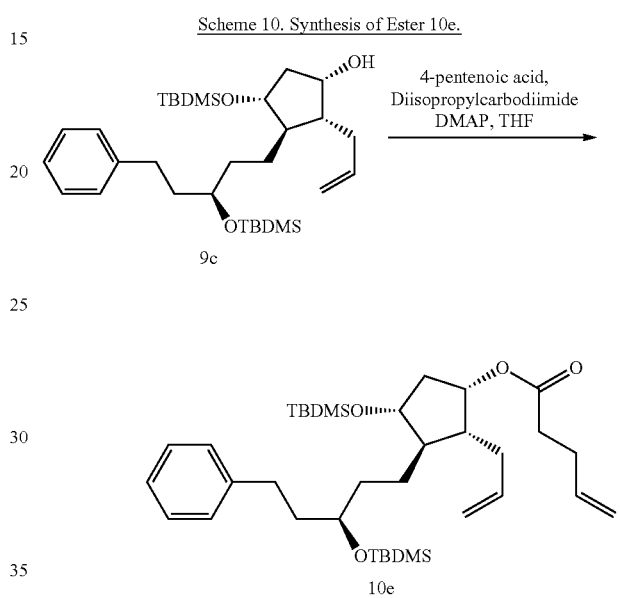

As shown in Scheme 10, a 100 mL 3-necked round-bottom flask equipped with a magnetic bar, a temperature probe, rubber septa, and a nitrogen gas inlet was charged at room temperature with 2.6 g (4.88 mmol) of alcohol 9c in 20 mL of THF, 0.12 g (1 mmol) of DMAP, 0.6 mL (5.4 mmol) of 4-pentenoic acid, and 0.9 mL (6 mmol) of N,N'-diisopropylcarbodiimide. The stirred mixture was heated at 40° C. for 24 h. TLC analysis indicated complete reaction. The reaction mixture was then diluted with 20 mL of MTBE and 20 mL of water. The layers were separated and the aqueous layer was back extracted with 30 mL of MTBE. The combined organic layers were washed with 40 mL of NaHCO$_3$, 40 mL of brine, dried over sodium sulfate, filtered, concentrated, and purified by column chromatography to obtain 2.7 g (90% yield) of ester 10e, confirmed by $^1$H NMR. Ester 10e can be used to prepare a 9-membered ring lactone, as shown in Scheme 11, below.

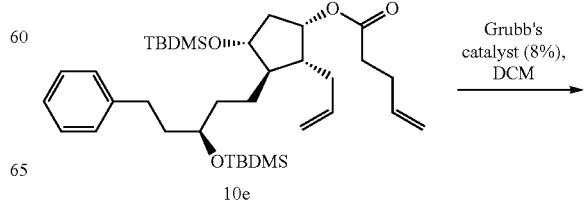

57

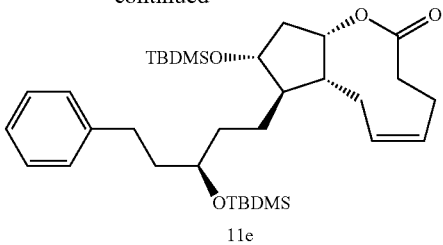

11e

A 1.0 L 3-necked round-bottom flask equipped with a magnetic bar, a temperature probe, rubber septa, and a nitrogen gas inlet was charged at room temperature with 2.7 g (4.4 mmol) of ester derivative 10e in 210 mL of DCM. The solution was purged with nitrogen for 30 min followed by the addition of 0.27 g of Grubb's catalyst. The stirred reaction mixture was heated at 40° C. for 18 h. TLC analysis indicated complete reaction. The reaction mixture was quenched with 5 mL of ethylamine and was stirred for 1 h. The reaction mixture was then diluted with 100 mL of MTBE and 200 mL of NaHCO$_3$. The layers were separated and the aqueous layer was back extracted with 100 mL of MTBE. The combined organic layers were washed with 200 mL of NaHCO$_3$, 200 mL of brine, dried over sodium sulfate, filtered, concentrated and purified by column chromatography to obtain 0.9 g (35.0% yield) of lactone derivative 11e, confirmed by $^1$H NMR.

Scheme 12. Synthesis of 9-Membered Ring Deprotected Lactone 12e.

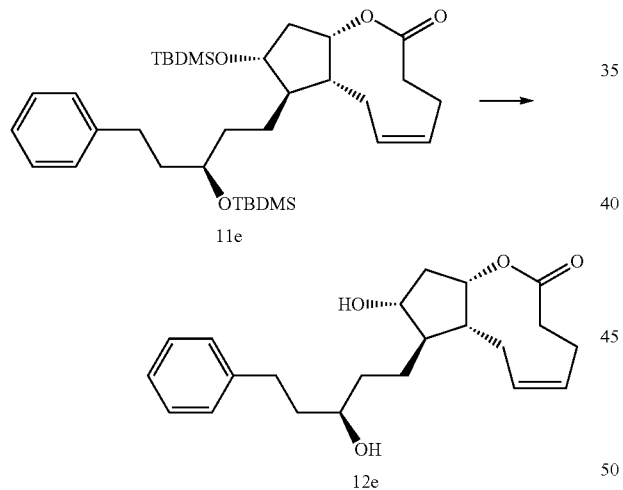

As shown in Scheme 12, a 50 mL 3-necked round-bottom flask equipped with a magnetic bar, a temperature probe, rubber septa, and a nitrogen gas inlet was charged at room temperature with 0.587 g (1.0 mmol) of lactone 11e in 25 mL of THF, 0.33 g (5.85 mmol) of ammonium hydrogen difluoride and 1.53 g (5.85 mmol) of tetrabutylammonium fluoride. The reaction mixture was heated at 40° C. for 24 h and TLC analysis indicated complete reaction. The mixture was diluted with 25 mL of MTBE and 50 mL of NaHCO$_3$. The layers were separated and the aqueous layer was back extracted with 25 mL of MTBE. The combined organic layers were washed with 40 mL of NaHCO$_3$, 40 mL of brine, dried over sodium sulfate, filtered, concentrated, and purified by column chromatography to obtain 0.3 g (83% yield) of deprotected lactone 12e, confirmed by $^1$H NMR.

58

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of preparing a prostaglandin or prostaglandin analog, the method comprising:
providing a compound of Formula (I):

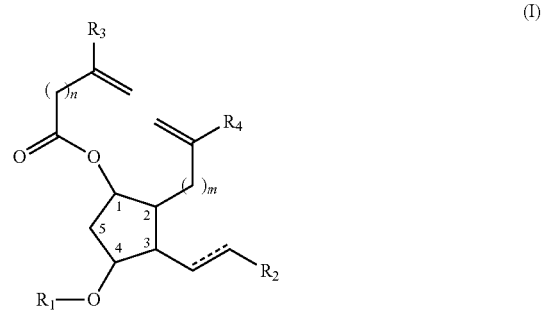

(I)

wherein:
n and m are integers between 0 and 4, wherein n+m is 3 or 4;
$R_1$ is H or a hydroxyl protecting group;
$R_2$ is H, alkyl or aralkyl, optionally wherein the alkyl or aralkyl group further comprises one or more alkyl or aryl group substituents;
$R_3$ and $R_4$ are independently H or alkyl;
and the substituents at carbons 1 and 2 of the cyclopentane ring are oriented cis to one another and trans to the substituent at carbon 3;
reacting the compound of Formula (I) with a transition metal carbene complex catalyst to perform a ring closing metathesis reaction, thereby forming a lactone; and
reacting the lactone with a nucleophile to form a ring-opened product, wherein said ring-opened product is a prostaglandin, prostaglandin analog or synthetic intermediate thereof, wherein said prostaglandin or prostaglandin analog has the formula:

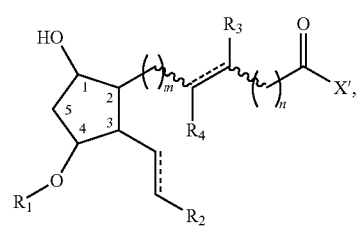

wherein m, n, $R_1$, $R_2$, $R_3$, and $R_4$ are as defined above; X' is selected from the group consisting of —OH, —SH, —NH$_2$, —O-alkyl, —O-aryl, —S-alkyl, —S-aryl, —NH-alkyl, —NH-aryl, —NH-aralkyl, —NH-sulfonyl-alkyl, —NH-sulfonyl-aryl, —N(alkyl)$_2$, —N(aryl)$_2$, and —N(alkyl)(aryl); and the substituents at carbons 1 and 2 of the cyclopentane ring are oriented cis to one another and trans to the substituent at carbon 3.

2. The method of claim 1, wherein the catalyst is a ruthenium benzylidene.

3. The method of claim 2, wherein the catalyst is benzylidene-bis(tricyclohexylphosphine)dichlororuthenium.

4. The method of claim 1, wherein n+m=4.

5. The method of claim 1, wherein the ring closing metathesis reaction is performed in an aprotic solvent.

6. The method of claim 5, wherein the aprotic solvent is dichloromethane.

7. The method of claim 1, wherein the nucleophile is selected from the group consisting of water, hydroxide, an alcohol, an alkoxide, an aryloxide, a thiol, a thiolate, an amine, an imide, and a sulfonamide, or a salt thereof.

8. The method of claim 7, wherein the nucleophile is an alkylamine.

9. The method of claim 8, wherein the alkylamine is ethylamine.

10. The method of claim 1, wherein reacting the lactone with a nucleophile is performed in an aprotic solvent.

11. The method of claim 10, wherein the aprotic solvent is tetrahydrofuran (THF).

12. The method of claim 7, wherein the nucleophile is an alcohol, an alkoxide, an alkoxide salt, or a mixture thereof.

13. The method of claim 12, wherein the nucleophile is 2-propanol, sodium 2-propoxide, or a mixture thereof.

14. The method of claim 1, further comprising removing one or more hydroxyl protecting groups.

15. The method of claim 14, wherein removing one or more hydroxyl protecting groups is performed prior to reacting the lactone with a nucleophile.

16. The method of claim 1, wherein the prostaglandin or prostaglandin analog is selected from the group consisting of bimatoprost, latanoprost, travoprost, tafluprost, unoprostone, prostaglandin $F_{2\alpha}$ ($PGF_{2\alpha}$), carboprost, fluprostenol, 13,14-dihydro-15-(2-benzothienyl)-15-pentanor $PGF_{1\alpha}$, and cloprostenol.

17. The method of claim 1, wherein the compound of Formula (I) is selected from the group consisting of:

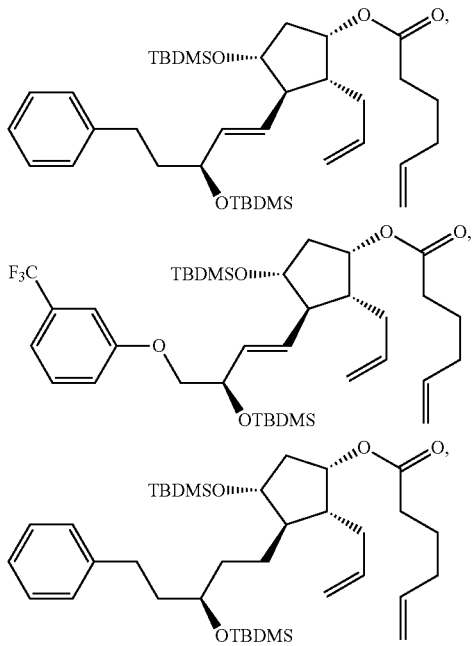

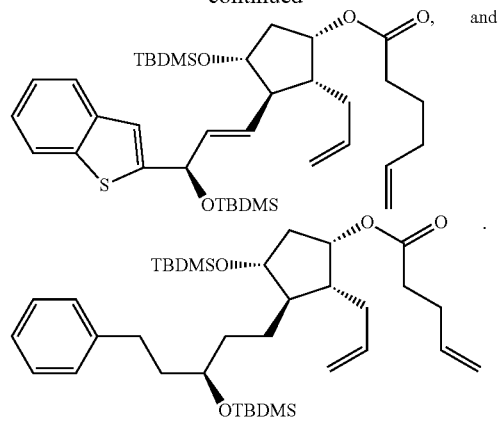

18. The method of claim 1, wherein the compound of Formula (I) is a compound of one of Formulas (Ia) or (Ib):

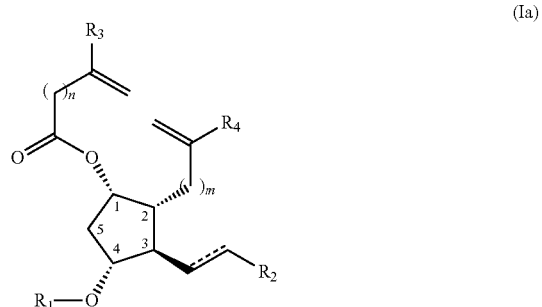

(Ia)

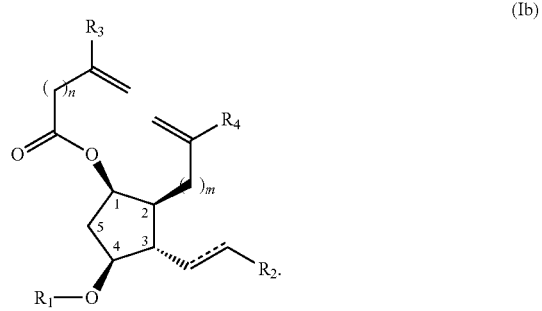

(Ib)

19. The method of claim 1, wherein n is 0, 2, or 3 and m is 1 or 4.

20. The method of claim 1, wherein n is 2 or 3 and m is 1.

21. A method of preparing a prostaglandin analog, the method comprising:

providing a compound of Formula (I):

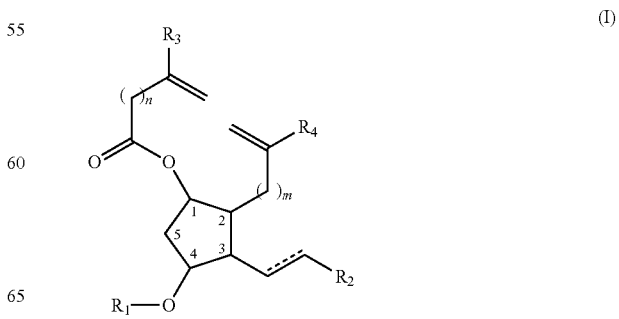

(I)

wherein:
n and m are integers between 0 and 4, wherein n+m is 3 or 4;
$R_1$ is a hydroxyl protecting group;
$R_2$ is H, alkyl or aralkyl, optionally wherein the alkyl or aralkyl group further comprises one or more alkyl or aryl group substituents;
$R_3$ and $R_4$ are independently H or alkyl; and
the substituents at carbons 1 and 2 of the cyclopentane ring are oriented cis to one another and trans to the substituent at carbon 3;
reacting the compound of Formula (I) with a transition metal carbene complex catalyst to perform a ring closing metathesis reaction, thereby forming a lactone;
reacting the lactone with a nucleophile to form a ring-opened product comprising a hydroxyl group;
oxidizing the hydroxyl group of the ring-opened product to form a ketone; and
removing the hydroxyl protecting group $R_1$, thereby forming a prostaglandin analog having the formula:

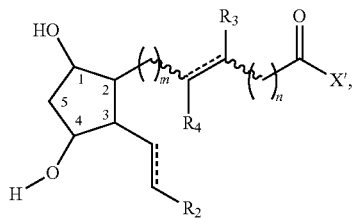

wherein m, n, $R_2$, $R_3$, and $R_4$ are as defined above and wherein X' is selected from the group consisting of —OH, —SH, —$NH_2$, —O-alkyl, —O-aryl, —S-alkyl, —S-aryl, —NH-alkyl, —NH-aryl, —NH-aralkyl, —NH-sulfonyl-alkyl, —NH-sulfonyl-aryl, —N(alkyl)$_2$, —N(aryl)$_2$, and —N(alkyl)(aryl).

22. The method of claim 21, wherein the prostaglandin analog is selected from sulprostone and limaprost.

* * * * *